US 10,709,858 B2

(12) United States Patent
McDonald

(10) Patent No.: US 10,709,858 B2
(45) Date of Patent: Jul. 14, 2020

(54) SEALING MECHANISM FOR ANAESTHETIC AIRWAY DEVICES

(71) Applicant: Airway Medical Limited, Dublin (IE)

(72) Inventor: Neil McDonald, Dublin (IE)

(73) Assignee: AIRWAY MEDICAL LIMITED, Dublin (IE)

( * ) Notice: Subject to any disclaimer, the term of this patent is extended or adjusted under 35 U.S.C. 154(b) by 181 days.

(21) Appl. No.: 15/507,341

(22) PCT Filed: Sep. 1, 2015

(86) PCT No.: PCT/EP2015/069925
§ 371 (c)(1),
(2) Date: Jul. 10, 2017

(87) PCT Pub. No.: WO2016/034572
PCT Pub. Date: Mar. 10, 2016

(65) Prior Publication Data
US 2019/0232008 A1      Aug. 1, 2019

(30) Foreign Application Priority Data

Sep. 4, 2014 (EP) .................................... 14183563

(51) Int. Cl.
*A61M 16/04* (2006.01)
*A61M 16/20* (2006.01)

(52) U.S. Cl.
CPC .... *A61M 16/0497* (2013.01); *A61M 16/0484* (2014.02); *A61M 16/0493* (2014.02); *A61M 16/0495* (2014.02); *A61M 16/208* (2013.01)

(58) Field of Classification Search
CPC .. A61M 16/00; A61M 16/04; A61M 16/0402; A61M 16/0431; A61M 16/0434;
(Continued)

(56) References Cited

U.S. PATENT DOCUMENTS 4,270,531 A * 6/1981 Blachly ............. A61M 16/0488
128/207.14
5,443,063 A * 8/1995 Greenberg ............ A61M 16/04
128/200.26
(Continued)

FOREIGN PATENT DOCUMENTS

JP         S35-297         1/1960
JP       2000051357        2/2000
(Continued)

OTHER PUBLICATIONS

Hawkins et al., "Fibreoptic intubation using the cuffed oropharyngeal airway and Aintree intubation catheter", Anaesthesia, 1998, 53, pp. 891-894 (Year: 1998).*
(Continued)

*Primary Examiner* — Timothy A Stanis
*Assistant Examiner* — Charles M Vivian

(57) ABSTRACT

The present invention is a multipurpose airway device adapted for insertion into the mouth of a patient. The airway device has an elongate, tubular airway body of substantially elliptical or substantially circular cross-section with a substantially straight section, the proximal end of which is adapted to function as an integral bite block; a curved distal section with a distal tip; and a central channel for accepting an intubation device. The airway device further includes a substantially oval-shaped detachable intraoral seal and a connector for facilitating attachment of breathing or anaesthesia equipment thereto. The invention also relates to an ETT locking device for attachment to the multipurpose airway device and a multipurpose airway pack including the multipurpose airway device and the ETT locking device.

27 Claims, 29 Drawing Sheets

(58) Field of Classification Search
CPC .......... A61M 16/0463; A61M 16/0488; A61M 16/049; A61M 16/0493; A61M 16/0497
See application file for complete search history.

(56) References Cited

U.S. PATENT DOCUMENTS

| | | | | |
|---|---|---|---|---|
| 6,679,257 | B1* | 1/2004 | Robertson | A61M 16/0488 128/201.26 |
| 6,736,139 | B1* | 5/2004 | Wix | A61M 16/0488 128/206.21 |
| 2003/0121520 | A1* | 7/2003 | Parker | A61M 16/06 128/206.21 |
| 2008/0156322 | A1* | 7/2008 | Isenberg | A61M 16/0488 128/200.26 |
| 2010/0170506 | A1* | 7/2010 | Pawels | A61M 16/0488 128/200.26 |
| 2013/0284181 | A1* | 10/2013 | Guerra | A61M 16/0463 128/207.14 |
| 2014/0216449 | A1* | 8/2014 | Chang | A61M 16/0495 128/202.16 |
| 2015/0157821 | A1* | 6/2015 | Manecke | A61M 16/0434 600/114 |
| 2016/0242872 | A1* | 8/2016 | Steffling | A61C 7/125 |

FOREIGN PATENT DOCUMENTS

| | | |
|---|---|---|
| JP | 2005535397 | 11/2005 |
| JP | 2007-531595 | 11/2007 |

OTHER PUBLICATIONS

Hammer et al., "Methods for Single-Lung Ventilation in Pediatric Patients", Anesth Analg, 1999, 89, pp. 1426-1429 (Year: 1999).*
ConvaTec Guedel Airway Product Data Sheet, 2013 (Year: 2013).*
Haas et al., "Endotracheal Tubes: Old and New", Respiratory Care, 2014, 59, pp. 933-955 (Year: 2014).*
Japanese Office Action dated Jul. 2, 2019 for corresponding Japan Patent Application No. 2017-512991 with English language translation.

* cited by examiner

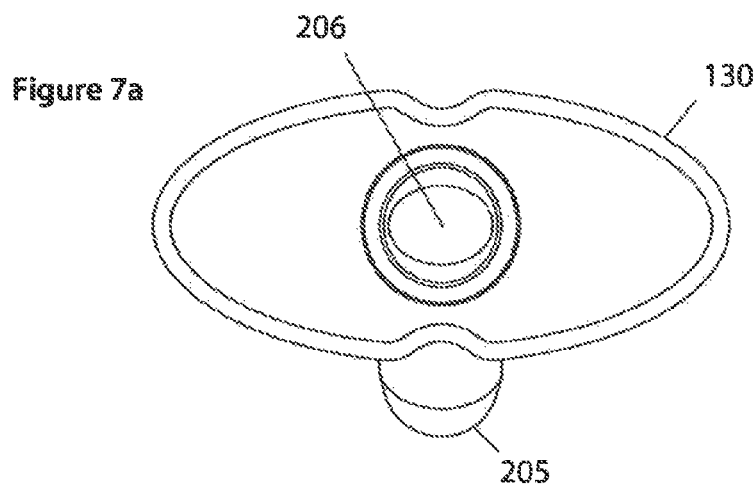
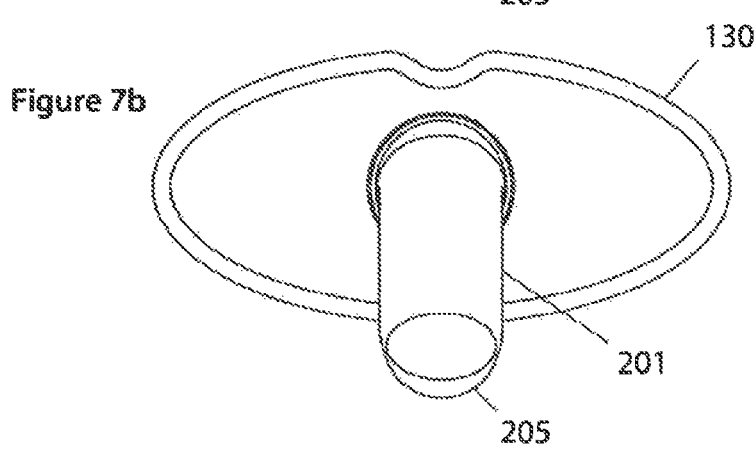
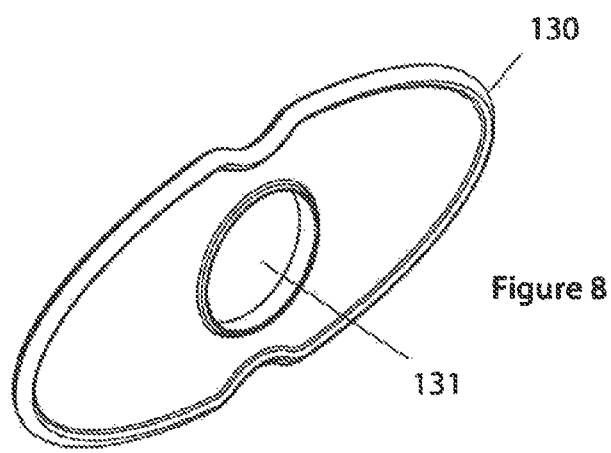

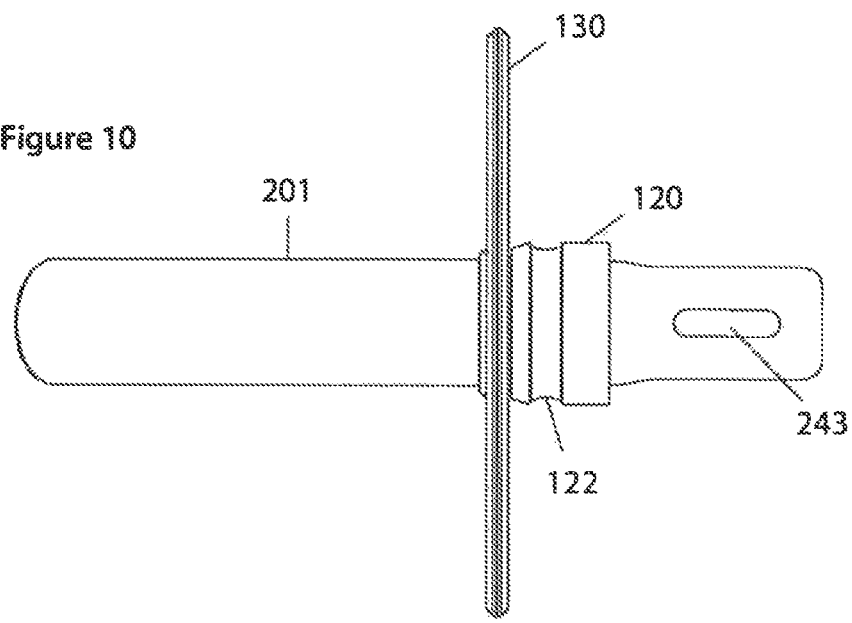
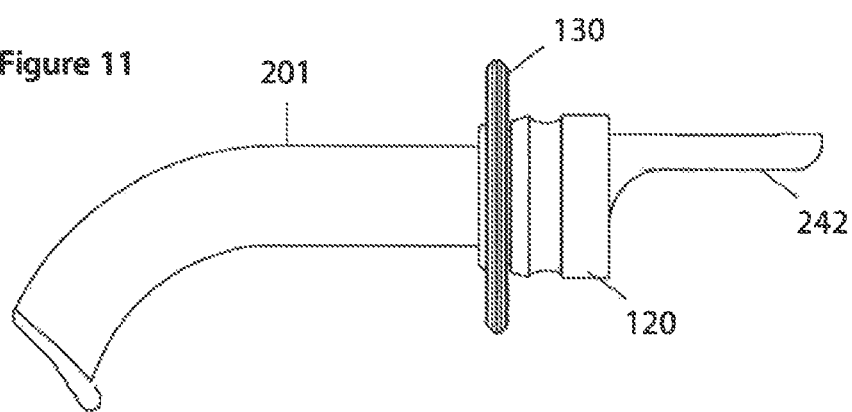

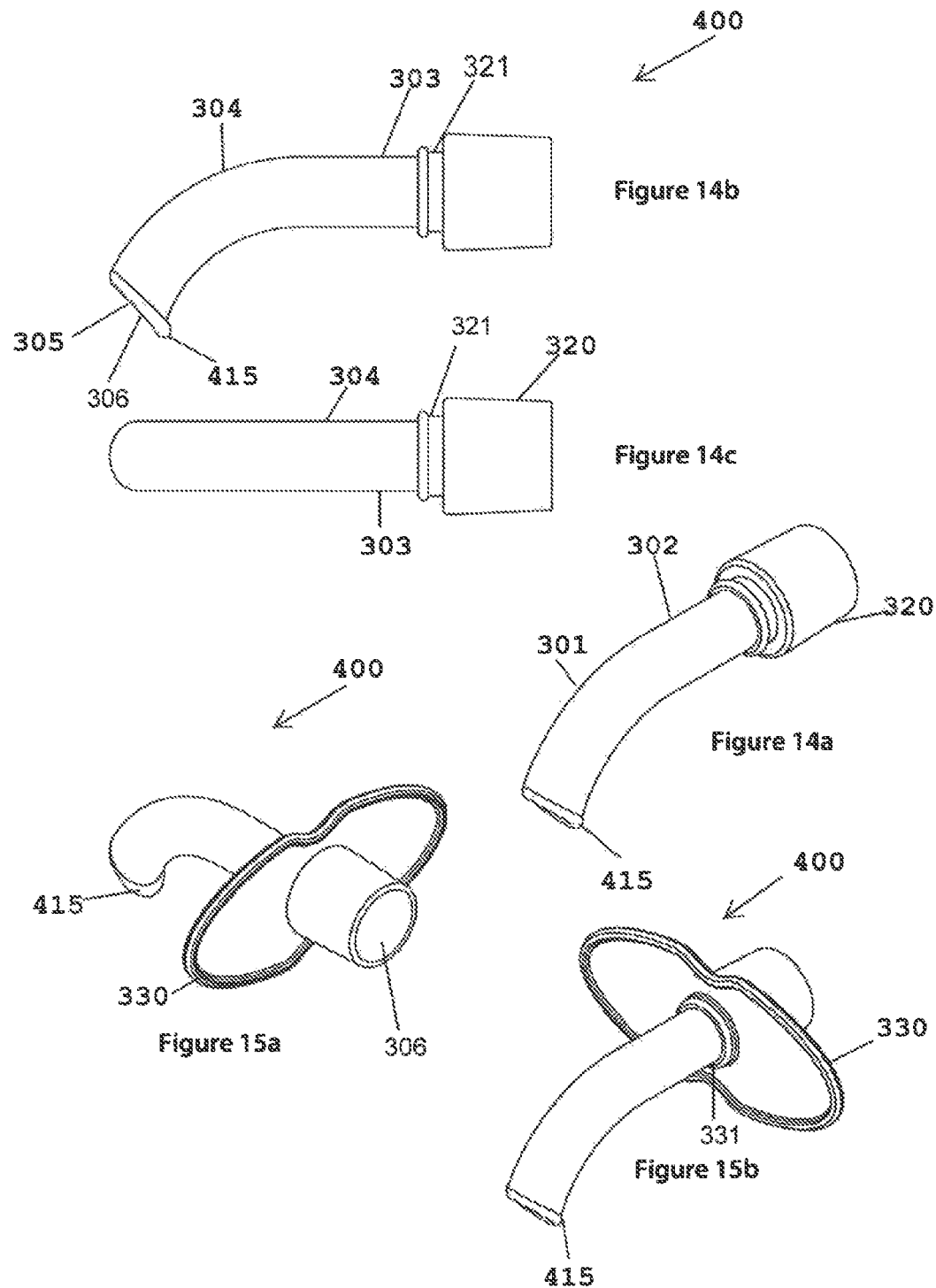

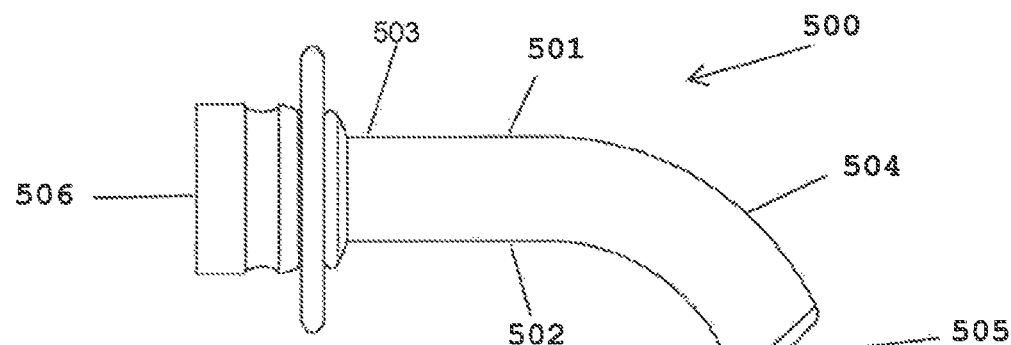
Figure 17
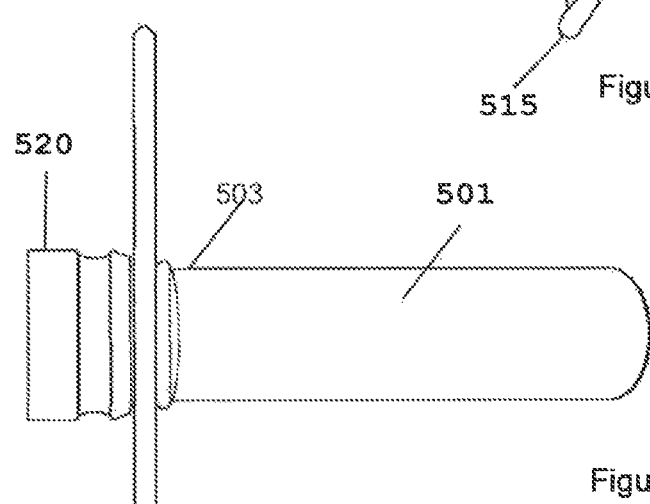
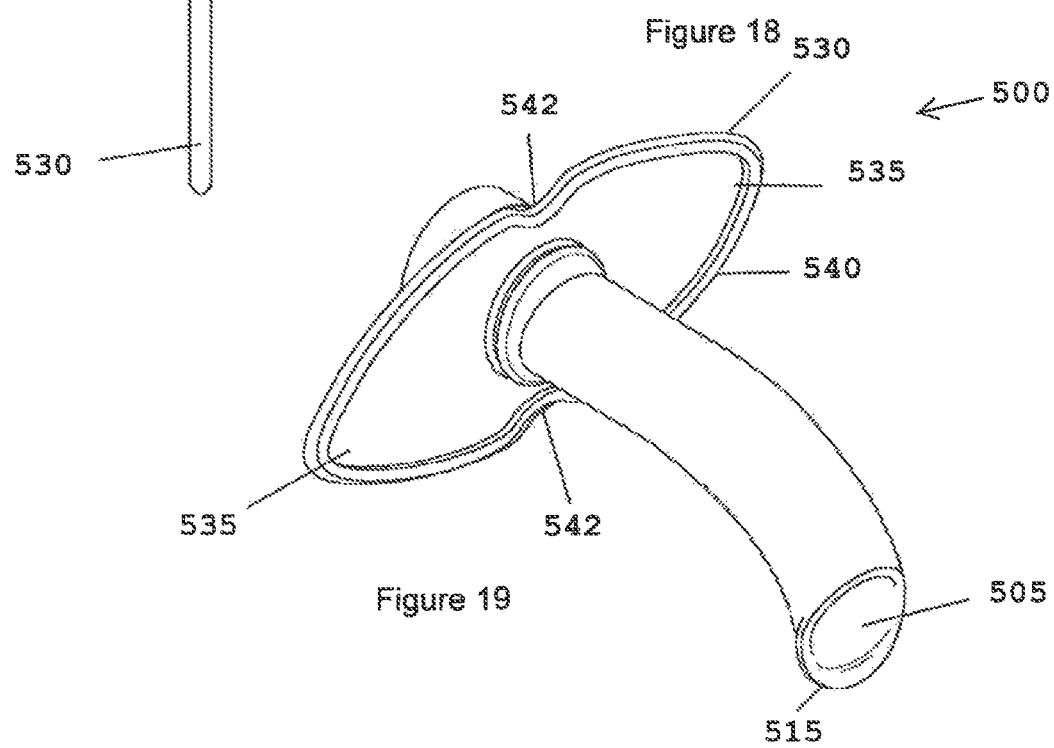
Figure 18
Figure 19

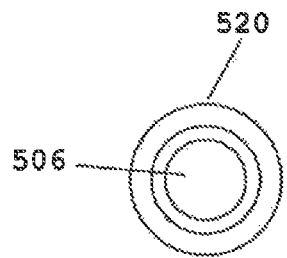
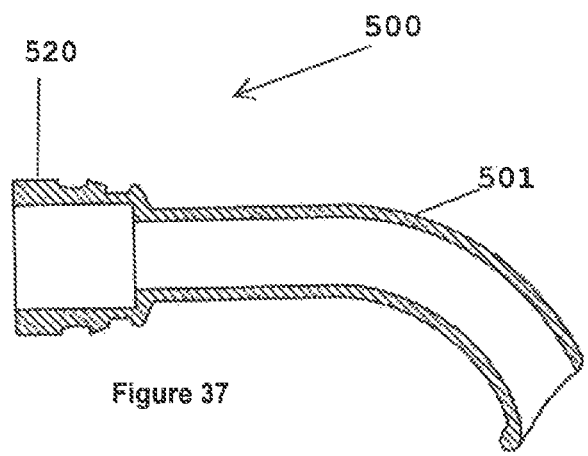
Figure 36  Figure 37
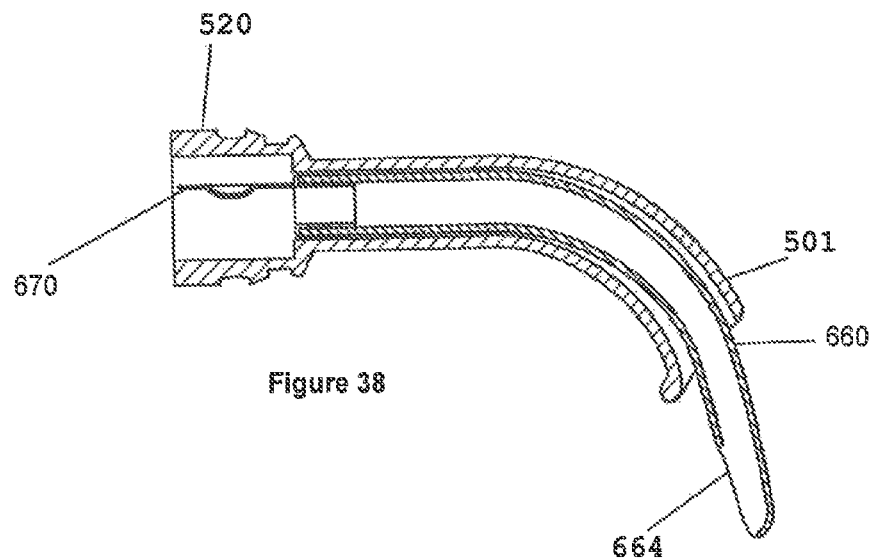
Figure 38

SEALING MECHANISM FOR ANAESTHETIC AIRWAY DEVICES

BACKGROUND OF THE INVENTION

1. Field of the Invention

The present invention relates to sealing mechanisms for anaesthetic airway devices and more particularly in relation to detachable, flexible, self retaining and self sealing devices which seal the inside of the mouth of a patient and can be used with all the commonly used anaesthetic airway devices.

Maintenance of a patient's airway is of paramount importance in anaesthesia. Difficulties or failures in managing the airway are the major factors underlying morbidity and mortality relating to anesthesia. With the loss of consciousness caused by general anaesthesia, there is loss of protective airway reflexes (such as coughing), loss of airway patency and sometimes loss of a regular breathing pattern due to the effect of anaesthetics, opioids, or muscle relaxants. To maintain an open airway and regulate breathing within acceptable parameters, some form of "breathing tube" is usually inserted in the airway after the patient is unconscious. Airway management is the medical process of ensuring there is an open pathway between a patient's lungs and the outside world, as well as ensuring the lungs are safe from aspiration.

2. The Related Art

A closed breathing circuit wherein the patient cannot breathe room air is required for anaesthesia for a number of reasons:
1. To control the concentration of oxygen, air and anaesthetic gases.
2. To facilitate positive pressure ventilation.
3. To scavenge anaesthetic waste gases.

At the interface between the breathing circuit and the patient, three mechanisms are commonly employed for sealing the circuit:
1. Anaesthetic face mask with or without an Oropharyngeal Airway (OPA).
2. Supraglottic airway devices such as the Laryngeal Mask Airway (LMA).
3. Cuffed endotracheal tube (ETT).

At all times during the course of anaesthesia and resuscitation, the anaesthetist needs to maintain a patent airway and be able to seal the breathing circuit for positive pressure ventilation. Positive pressure ventilation can be delivered either manually using a bag and valve technique or by using a mechanical ventilator.

When using an anaesthetic face mask the anaesthetist has to maintain a patent airway and at the same time seal the mask around the patient's mouth and nose with or without an oropharyngeal airway (OPA). Bag Mask Valve ventilation is difficult in more than 5% of patients and impossible in 0.16%.

A cuff inflated with air seals the LMA. However it is frequently difficult to achieve a seal and this leads to more air injected into the cuff. Sore throat occurs in up to 40% of patients as a result of these high cuff pressures. Serious nerve palsies and laryngeal injuries have been reported after LMA use.

Cuffed endotracheal tubes are sealed by inflating air into the cuff located in the trachea. Intra-operatively cuffs can malfunction or rupture. Uncuffed ETT's are often preferred in children to avoid injury to the trachea. Deflating the cuff of an ETT while the patient is still deeply anaesthetized can facilitate a smoother extubation with less coughing and gagging because an inflated cuff is very stimulating. A "Deep Extubation" is used after certain surgeries where the ETT is removed while the patient is still deeply anaesthetized and before the return of airway reflexes. In unstable hypotensive critically ill mechanically ventilated patients in Intensive Care the constantly inflated cuff of the ETT can cause ischaemic damage to the mucosa of the trachea.

Bag mask valve ventilation is a "Hands On" technique because the anaesthetist has to concurrently maintain a patent airway and seal the mask on the patient's face. Moving the mask and OPA to restore a patent airway disrupts the seal and vice versa.

In practice, this means that the anaesthetist has to actively maintain the patient's airway and seal the breathing circuit for the duration of the anaesthetic. In the past, techniques which involved the use of special harnesses (e.g. Clausen harness) were sometimes employed in an attempt to make the procedure "hands free" but were usually not successful because of the way the harness pulled the mask down and pushes back on the lower jaw causing airway obstruction.

Prior to the introduction of the Laryngeal Mask Airway (LMA) in 1988, general anaesthesia for minor operations was conducted using a bag and mask technique with or without an OPA such as a Guedel airway in a spontaneously breathing patient (approximately 30-40% of general anaesthetics). Today the LMA is the most commonly used airway device for short general anaesthetics. The LMA is "Hands Free".

However the LMA is more invasive than an OPA and for example there is a very high incidence of sore throat after it's use. Injuries to laryngeal structures or nerves occasionally occur. In order to place an LMA, the anaesthetist must give a large enough dose of an induction agent such as propofol and or a muscle relaxant in order to suppress the Gag and Laryngeal closure reflexes. This frequently results in marked hypotension and apnoea in frail elderly patients and those with cardiovascular and respiratory disease. In contrast an OPA can be inserted at a lighter level of anaesthesia and so allow for a more gradual induction of anaesthesia.

Anaesthesia using an ETT is also "Hands Free" in that the Anaesthetist is free to attend to other tasks once the airway is secured.

Airway devices that are positioned outside a patient's larynx are collectively known as supraglottic airways. Oropharyngeal airways are a type of supraglottic airway which only project as far as the oropharynx. For example, Guedel airways have been used for more than 50 years to help to maintain an open airway during general anaesthetics and resuscitation and are the most commonly used type of oropharyngeal airway. A Guedel airway helps in the formation of a seal between a patient's face and a face mask, provides an air channel to the patient's pharynx, facilitates jaw thrust and pushes the patient's tongue forward to prevent the tongue from covering the epiglottis. Many anaesthetists consider it good practice to additionally place a bite block in the mouth of anaesthetised patients in case the patient bites down when waking up, e.g. during removal of an endotracheal tube at the end of a case. Biting down is a common cause of dental damage and can in some cases cause negative pressure pulmonary oedema.

Although commonly used in anaesthetics, Guedel airways have a number of shortcomings. They do not connect to the breathing circuit, the bite block is hard and the distal end has a sharp edge which can cause trauma to teeth and soft tissues in the mouth. Guedel airways can be tricky to place because the distal end glottal surface is sharp, straight and hard, and tends to catch on the tongue. The recommended way to place the Guedel is to start with it upside down and turn it 180° when the distal end has reached the oropharynx, i.e. when the tip reaches the back of the throat.

Furthermore, Guedel airways are temporary devices and are rarely used for longer than 2 or 3 minutes during anaesthesia, after which they are usually replaced by other supraglottic airways such as a laryngeal mask airway (LMA) or an endotracheal tube (ETT). Advanced airway skills are required when using these devices. For example, sometimes the laryngeal closure reflex is activated immediately after LMA placement in the non-paralysed patient. An inexperienced or novice airway management operative can assume that mal-position of the device has occurred and thus may remove the LMA or aggressively "bag" the patient causing stomach distension. If the gag reflex is activated, the vomiting reflex may also be activated. Therefore depression of pharyngeal reflexes by general anaesthesia is typically required when using such devices.

In those cases where the anaesthetist cannot maintain an adequate airtight seal during bag mask valve (BMV) ventilation, for example when the patient has facial hair such as a beard or moustache, is edentulous (lacking teeth), obese, has facial burns or other facial skin condition or trauma, the anaesthetist would typically have to rush general anaesthetic induction by prematurely placing either an LMA or ETT. BMV ventilation is also difficult for an anaesthetist with small hands looking after a big patient and some patients are mask phobic (e.g. due to claustrophobia) and will not tolerate a face mask for pre-oxygenation prior to induction of general anaesthesia.

Sometimes the depth of anaesthesia is determined by the type of airway device used rather than the requirements of the type of surgery. It is considered prudent now to minimise exposure to anaesthesia, i.e. depth and total duration of anesthesia for all patients and particularly for the very young and the elderly.

A number of ventilation systems have been proposed as alternatives to endotracheal intubation or the use of a face mask. For example, U.S. Pat. No. 4,270,531 discloses a U-shaped bite block fitted about the exterior of an airway tube having the same general configuration as conventional oropharyngeal tubes such as the Guedel airway. The bite block has vertically separated upper and lower tooth- or gum-engaging surfaces and a peripheral rim to fit against the outer surfaces of the teeth or gums of the patient and inside the lips. When inserted into the patient's mouth, the posterior tube portion extends above the tongue to the upper throat, preventing the tongue from blocking the throat. There are several disadvantages to this. For example, it would most likely have to be positioned like a Guedel airway, i.e. upside down first. As the device is bulkier than a Guedel airway, this would be difficult. There would be a considerable risk of trauma to soft delicate pharyngeal structures and the bite block could cause hard trauma to teeth. Additionally, the U-shaped bite block is contoured to the shape of the upper and lower jaws. The opening between the upper and lower jaws is much greater than that covered by this device. During positive pressure breaths, gas escapes from between the jaws and behind or lateral to the device. The mouth can only be sealed by applying external pressure over the cheeks and lips. Additionally the device disclosed in U.S. Pat. No. 4,270,531 is not capable of facilitating fibreoptic intubation (FOI), i.e. it is not the correct shape for functioning as an airway for FOI nor does it allow for administration of 100% oxygen and positive pressure breathing during FOI. Additionally it cannot be used to seal laryngeal mask airways or endotracheal tubes.

WO 2005/097245 discloses a respiratory mask having an intraoral mouthpiece configured to fit the natural shape of the gums and inside of the lips of persons to be ventilated. However, this intraoral mouthpiece is not configured to seal the mouth opening, for example during positive pressure breathing. The intraoral mouthpiece is smaller than the opening between the upper and lower jaws. During positive pressure ventilation, gas escapes around the posterior margins and pushes between the mouth piece and the cheeks and attempts to escape from the corners of the mouth. A seal is achieved by applying external pressure over the cheeks. In addition due to it's contoured shape the intraoral mask tends to pop out of the mouth. The intraoral mouthpiece has a central orifice which feeds into a tubular extension having a reinforced collar. The collar allows a healthcare provider to handle and position the respiratory mask. A flexible oropharyngeal airway may be used in combination with the intraoral mouthpiece either by attachment with a recess in the inner wall of the intraoral mouthpiece or by slidable insertion through the tubular extension. This is not intuitive and may pose problems for the occasional user. Due to the flexibility of both the intraoral mouth piece and the oropharyngeal airway the Anaesthetist lacks control over airway structures such as the tongue when they are used combined together. The respiratory mask disclosed in WO 2005/097245 cannot act as a bite block. Additionally, it cannot be used to facilitate FOI nor to allow for administration of 100% oxygen and positive pressure breathing during FOI. Additionally, it cannot be used for positive pressure ventilation via an uncuffed endotracheal tube. Additionally it cannot seal a laryngeal mask airway (LMA) when the LMA cuff has failed to seal the airway.

Despite the advances of the prior art described hereinabove, there is a need to provide an airway device which makes the process of anaesthesia for minor procedures less invasive and allows such anaesthesia to be conducted at a lighter level and "hands free", and an airway device that is more easily inserted, can be placed while the patient is awake, allows passage of medical devices such as an ETT or fibreoptic bronchoscope (FOB) therethrough and incorporates a bite block. Additionally the intraoral seal when used with a specially adapted laryngeal mask airway (LMA) or endotracheal tube (ETT) can provide an alternative sealing mechanism for positive pressure ventilation.

It is an object of the present invention to provide a device and method that seek to alleviate the aforementioned problems.

SUMMARY

The invention is more particularly defined in the appended claims 1 to 31.

Thus according to a first aspect, the invention provides a multipurpose airway device adapted for insertion into the mouth of a patient, said airway device comprising:
(a) an elongate, tubular airway body of substantially elliptical or substantially circular cross-section, the airway body having:
a substantially straight section, the proximal end of which is adapted to function as an integral bite block;
a curved distal section with a distal tip; and a central channel for the passage of oxygen and anaesthetic gases and for accepting an intubation device;

(b) The central channel of the MPA has a greater anteroposterior diameter than an OPA of the Guedel type and this keeps the tongue away from the posterior wall of the pharynx and helps to keep the patient's airway patent.

(c) a connector for facilitating attachment of breathing or anaesthesia equipment thereto, wherein the connector is attached to the proximal end of the airway body and has a groove on its external surface, wherein the groove forms a circular channel for accepting the intraoral plate.

As used herein, the term "distal" as it refers to the elongate, tubular airway body refers to the part of the airway body which in use leads as the device is introduced into the patient's mouth and is further from the clinician deploying the device, whereas the term "proximal" refers to the other end of the airway body which in use is nearer the clinician.

An airway device that when used in combination with an endotracheal tube has the following advantages:

Allows the endotracheal tube to be secured in position independent of the tie or tape used to secure the airway device to the patient;

Provides a Bite-Block;

Prevents kinking of the endotracheal tube;

Provides a means for supraglottic ventilation at the time of extubation;

Provides a means for deep extubation.

An airway device is provided that is both self retaining and self sealing for cardiopulmonary resuscitation.

An airway device is also provided that can prevent and or treat all of the most common Airway emergencies:

Difficult and Impossible Mask Ventilation;

Difficult and Impossible Mask Ventilation and Difficult Intubation;

Biting Down;

Inadequate ventilation after extubation.

The detachable, flexible, self sealing and self retaining plate can be mounted on a variety of airway devices including oral and oropharyngeal airways, supraglottic airways (e.g. LMA) and endotracheal tubes. It can be used for anaesthesia, resuscitation and various forms of non invasive ventilator support. When the plate is mounted on a specially adapted LMA or ETT it can provide an alternative sealing mechanism to an inflated cuff for positive pressure ventilation;

The detachable, flexible, self-sealing and self retaining plate is essentially flat and a greater cross-sectional area than the mouth opening. The shape corresponds to the mouth opening when the mouth is half open. Each end is arrow shaped like the corner of the mouth when the mouth is open to aid placement.

The plate has a reinforced rim around the perimeter. A second rim surrounds the central aperture. The two rims resist deformation. The plate is a one piece construction of polyvinyl chloride, polyurethane, silicone or other elastomeric material possessing the correct properties of elasticity, stiffness, resilience and flexibility such that the plate is self retaining and self sealing. Elasticity allows it to be fitted and retained in position on airway devices. Elasticity allows the ends to be compressed between thumb and forefinger for placement inside the cheeks.

The plate is self-retaining inside the mouth because it's cross sectional area is greater than the mouth opening and because of it's essentially flat shape and because of it's sufficiently high stiffness and yield strength. It resists further deflection and so does not pop out of the mouth. In effect, the plate has a bending stiffness low enough to enable deflection by point load application for insertion, but stiff enough to limit the deflection when placed in the mouth where it has effectively a distributed load applied by the positive pressure and is also restrained by the mouth.

The plate is self-sealing because of its resilience, in that it is quickly and constantly trying to return to its original shape. In this way it forms a dynamic seal of the inside of the mouth in that it continuously follows variation in the surface of the mouth that it is sealing. Thus it continues to seal during periods of positive pressure ventilation when the mouth may undergo small changes in size and shape during the different phases of the respiratory cycle. Not only does it maintain a seal as the mouth opening changes size and shape but the sealing effect is enhanced by the gas pressure forcing the seal against the inside of the cheeks in a similar way that water in a bath pushes down on the plug in the plug hole. The chosen elastomeric material has a high elastic limit and doesn't display plasticity in its working range.

The lips function as a purse string largely because of the bulk of the orbicularis oris muscle even when it is relaxed and not contracting. The rim around the perimeter of the plate resists distortion and when in place in the vestibule of the mouth sits outside the orbicularis oris muscle and so retains the plate even during positive pressure breaths. The plate is further supported in position in the vestibule of the mouth between the lips and cheeks and the gums and teeth by the airway device traversing and firmly gripped in the central aperture of the plate. A plate with an appropriately sized central aperture is required for each airway device. The cut-out in the midline at the top and bottom of the plate accommodates the top and bottom frenulum.

Between the perimeter rim and the rim surrounding the central aperture the plate is soft and very flexible. During positive pressure ventilation breaths, the plate seals the mouth opening by adhering to the soft moist and smooth inner mucosa of the cheeks and lips. The plate contributes to jaw thrust because it resists displacement. When the plate is in position in the vestibule of the mouth it is forced by the cheeks to adopt the contour of the inside of the cheeks. In resisting displacement and because the upper jaw is fixed and not mobile, the plate exerts a pulling force on the lower jaw. The intraoral plate does not seal the large opening between the upper and lower jaws but rather seals the mouth from the inside.

The width of the vestibule of the mouth is much greater than the width of the mouth opening and this allows for the width of the plate to be much greater than the maximum width of the mouth opening. Thus the corners of the mouth are particularly well sealed and no gas leaks from the corners of the mouth.

The airway devices e.g. Oral Airway, OPA, LMA or ETT can be used with or without the self retaining, self sealing plate. If not originally mounted on the airway device prior to its insertion into the patient, the plate can be fitted from the proximal end of the airway device and pushed down into position in the vestibule of the mouth between the lips/cheeks and teeth/gums.

When not required to seal the airway the plate can be positioned on the airway device outside the lips and rotated 90 degrees so as not to obstruct the mouth.

The self retaining and self sealing intraoral plate is detachable allowing for different sized plates to be fitted to different sized airway devices. This allows for variation in patient anatomy.

There is no inside, outside, upside or downside to the self retaining and self sealing plate. It is inherently intuitive as to how it fits on the airway device. This means that in an emergency no time is lost and also that the plate cannot be fitted the wrong way round.

The self retaining and self sealing plate according to the invention makes the anaesthetist's job easier, increases patient safety and results in basic airway management being easy to achieve for someone who is not an expert in airway skills.

Preferably, conventional nasal occluding means such as a nose clip are used in combination with the self retaining and self sealing plate to permit positive pressure ventilation of a patient. Alternatively, rather than a nose clip being used, an anesthetist or anesthetist's assistant could pinch the patient's nostrils closed.

In a preferred embodiment, the multipurpose airway device is a multipurpose oral airway device, wherein the curved distal end of the airway body substantially conforms to the curvature of the palate but does not extend into the pharynx. In an alternative embodiment, the multipurpose airway device is a multipurpose oropharyngeal airway device, wherein the curved distal end of the airway body substantially conforms to the curvature of the part of the pharynx between the soft palate and the upper edge of the epiglottis.

The substantially flat oval-shaped detachable intraoral plate is adapted to fit between a patient's gums and teeth and lips and cheeks. The airway body is adapted to pass through the central aperture of the detachable intraoral plate. The detachable intraoral plate can be fitted to the multipurpose airway device from either the proximal end via the connector or from the distal end via the airway body. The airway supports the plate during positive pressure breaths. The fact that the detachable intraoral plate can be fitted from the proximal end of the multipurpose airway device ensures that in the event the anaesthetist is unable to achieve a seal between a face mask and the patient's face when using the multipurpose airway device as an oropharyngeal airway, the anaesthetist can fit the detachable intraoral plate while the airway device is in place in the patient's mouth. This is particularly beneficial should the patient be biting down at the time.

The detachable self retaining and self sealing plate has at least one axis of symmetry, preferably two axes of symmetry. In a preferred embodiment, the shape of the detachable intraoral plate resembles an infinity symbol, i.e. an oval with triangular cut-outs at the top and bottom. It is arrow or triangular shaped at each end.

In use, the detachable intraoral self retaining and self sealing plate provides a substantially airtight seal between the airway body and the inside of a patient's mouth, in particular during positive pressure breathing. During a positive pressure breath gas emitting from the distal end of the airway pushes up against the plate increasing the sealing effect in the same way as water pressure in a bath forces the plug into the plug hole. An airtight seal is provided even in the absence of teeth in a patient. This facilitates positive pressure ventilation where a good seal cannot be made between the mask and a patient's face, for example due to patient obesity, a skin condition, facial deformity, lack of teeth or the presence of a beard.

Because it is self retaining and self sealing it is also "Hands Free". The airway can be further secured with a simple elasticated tie looped around the patient's neck. Such a tie does not exert external pressure on the lower jaw and does not hinder jaw thrust.

The groove for accepting the detachable intraoral self retaining and self sealing plate surrounds the circumference of the connector such that the plate can be rotated with respect to the airway body within the groove on the connector. This possibility of rotation is particularly useful when the patient has facial asymmetry, for example after head and neck cancer surgery, whereby one side of their mouth drops significantly. This group of patients frequently require multiple operations and because of their prior facial disfigurement are frequently difficult to BMV ventilate, i.e. it is often difficult to achieve a seal on such patients using prior art face masks. The fact that the detachable intraoral self retaining and self sealing plate can be rotated on the connector and about the main axis of the airway body ensures that the plate can be aligned with the mouth opening to seal the mouth and maintain an airtight seal between the connector and the detachable intraoral self retaining and self sealing plate.

The airway body preferably has a hard internal surface, i.e. the airway body is preferably made of hard material on the inside, to maintain the lumen even if the patient bites down. Thus the proximal end of the substantially straight middle section of the airway body acts as an integral bite block. Preferably, the airway body is made of a polymer selected from among medical grade polyethylene, polypropylene, polyvinylchloride and polycarbonate, preferably polyethylene.

The underside of the straight middle section of the airway body is provided with a glottal surface to assist in preventing the tongue from obstructing the pharynx, i.e. the portion of the airway body in contact with the tongue is curved. The profile of the glottal surface is horizontal where the glottal surface is in relative position with the tongue. The profile then sweeps down substantially conforming to the contours of the mouth to increase its area of contact with the tongue.

The leading edges of the distal end of the airway body are rounded to minimise trauma to the anatomy, for example to minimise damage to delicate oral and pharyngeal tissues. In the oropharyngeal airway device, the glottal surface (i.e. underside) of the distal end is provided with a rounded lip at the distal tip which aids placement of the device into a patient's pharynx. The lip allows the device to slide over the patient's tongue during placement minimising trauma to the tongue and oropharynx.

The curved underside of the distal end of the airway body aids placement of the multipurpose airway device into the patient, as does the glottal lip, when present. The multipurpose airway device can thus be placed without turning it upside down first as would be required with a standard airway device, e.g. a Guedel airway, which has a sharp, straight and hard distal end which tends to catch on the tongue.

The airway body and detachable intraoral self retaining and self sealing plate may each independently be made in different sizes to accommodate varied patient groups, such as infants, children, women, men and adults of different sizes. Preferably, the detachable intraoral seal and airway body are each independently provided with a size identifier such as an integer from 1 to 5, e.g. 3. This size identifier represents a similar sizing system to the Guedel and the LMA sizing system wherein size 1 is for an infant, 2 for a child, 3 for a small adult, 4 for an adult and 5 for a large adult.

The multipurpose airway device according to the invention is suitable for use in conjunction with breathing equipment such as a one-way valve, or a bag and valve for positive pressure ventilation. Additionally, the multipurpose airway device is suitable for use in conjunction with anaesthetic equipment.

Without the detachable intraoral plate the multipurpose airway device can be used in the same manner as a traditional oropharyngeal airway device such as a Guedel airway but without the need to turn the device during placement.

The distal tip of the oropharyngeal airway body can be advanced or withdrawn into or out of the patient's pharynx to allow for the multipurpose oropharyngeal airway device to be advanced gradually as the level of anaesthesia deepens without activating the patient's gag reflex.

The radius of curvature of the airway body is preferably in the range of from approximately 20 mm to approximately 50 mm, e.g. 35.50 mm or 35.75 mm.

In one embodiment, the multipurpose airway device is suitable for a child and has circular internal and external profiles, i.e. has a circular cross-section. In this embodiment, the internal diameter of the airway body is preferably in the range of from approximately 7 mm to approximately 40 mm, e.g. 11.75 mm. In another embodiment, the multipurpose airway device is suitable for an adult, is larger than the child-suitable version and has an elliptical cross-section. In this embodiment, the external conjugate diameter of the airway body is in the range of from approximately 15 mm to approximately 50 mm, e.g. 18.50 mm and the external transverse diameter of the airway body is in the range of from approximately 15 mm to approximately 50 mm, e.g. 23.50 mm. The internal diameter of the adult multipurpose airway device is sufficient to allow passage of a size 8 (standard Male adult size) ETT and is preferably in the range of from 10 mm to approximately 45 mm, e.g. 15.5 mm.

The diameter of the connector also varies for the adult and child version. Preferably, the external diameter of the adult connector is in the range of from approximately 15 mm to approximately 50 mm, e.g. 30 mm, and the internal diameter of the adult connector is in the range of from approximately 10 mm to approximately 45 mm, e.g. 23 mm. The connector on the adult device has a second groove which provides a circular channel for accepting tie material. The reason for the difference in cross-section between the adult and child versions is in the method of interfacing with the standard breathing aids. By "standard breathing aids" is meant breathing aids conforming to the ISO standard for anaesthetic and breathing aids. The child size connectors are of a reduced outer diameter as they are fitted to a breathing circuit as a male connector, whereas the larger diameter adult size connector acts as a female connector when fitting to the breathing circuit. Key dimensions are driven by the ISO 5356.1.2004 standard for Anaesthetic & Respiratory Equipment-Conical Connectors.

The multipurpose airway device according to the invention is suitable for use in, but not limited to, the following: maintenance of a "Hands Free" patient airway; difficult airway situations, e.g. difficult bag mask ventilation situations; anaesthesia; resuscitation; pre-oxygenation of mask-phobic patients; airway maintenance and airway rescue during sedation procedures, especially when sedation is too deep, i.e. when the doctor has given more drug than intended and respiration has to be assisted; a combined airway and bite-block for the passage of other medical devices such as a gastroscope under sedation; guide and passageway for medical devices such as ETT and FOB; gas induction; and supraglottic ventilation at extubation.

A standard definition of "difficult airway situations" cannot be identified in the available literature but can be defined as the clinical situation in which a conventionally trained anesthesiologist experiences difficulty with facemask ventilation of the upper airway, difficulty with tracheal intubation, or both. The difficult airway represents a complex interaction between patient factors, the clinical setting, and the skills of the practitioner.

A difficult airway can include, but is not limited to the following:
1. Difficult facemask or supraglottic airway (SGA) ventilation (e.g., LMA, intubating LMA [ILMA], laryngeal tube): It is not possible for the anesthetist to provide adequate ventilation because of one or more of the following problems: inadequate mask or SGA seal, excessive gas leak, or excessive resistance to the ingress or egress of gas. Signs of inadequate ventilation include (but are not limited to) absent or inadequate chest movement, absent or inadequate breath sounds, auscultatory signs of severe obstruction, cyanosis, gastric air entry or dilatation, decreasing or inadequate oxygen saturation ($SpO_2$), absent or inadequate exhaled carbon dioxide, absent or inadequate spirometric measures of exhaled gas flow, and hemodynamic changes associated with hypoxaemia or hypercarbia (e.g., hypertension, tachycardia, arrhythmia).
2. Difficult SGA placement: SGA placement requires multiple attempts, in the presence or absence of laryngeal or tracheal pathology.
3. Difficult laryngoscopy: It is not possible to visualize any portion of the vocal cords after multiple attempts at conventional laryngoscopy
4. Difficult tracheal intubation: Tracheal intubation requires multiple attempts, in the presence or absence of laryngeal or tracheal pathology; and
5. Failed intubation: Placement of the endotracheal tube fails after multiple attempts.

A traditional respiratory mask includes a fixed domed or cup-shaped device that fits over the mouth and nose of a wearer. The edge of this dome or cup fits against the face of the wearer. The multipurpose airway device according to the invention avoids the need for pressure contact between a patient's facial skin and the mask. This is beneficial in some cases as pressure could cause injury to the patient, e.g. after facial trauma, burns, skin infection or the like.

Prior to the introduction of LMA's in 1988, general anaesthesia for minor surgical procedures was often conducted using a face mask and oropharyngeal airway technique. Attempts to free the anaesthetist from direct contact with the patient by using devices such as a Clausen harness often failed because pressure exerted by the harness on the lower jaw tends to cause airway obstruction. An LMA is more invasive for the patient than the oropharyngeal airway according to the invention and frequently causes postoperative sore throat. In addition, full general anaesthesia is required in order to place an LMA.

In many minor procedures the depth of anaesthesia required is determined by the airway device used rather than what is required for the procedure. There is increasing concern that general anaesthesia, at least for the very young and the elderly, may lead to permanent neurological impairment. The multipurpose airway device according to the invention offers a simple alternative to airway devices requiring general anaesthesia for short minor procedures such as examination under anaesthesia and rigid cystoscopy, especially when used in combination with a simple nose clip and chin prop.

Airway problems are more common at time of extubation (e.g. removal of an ETT) than at induction of anaesthesia. When a deep extubation is desired the multipurpose airway device according to the invention can be left in place after extubation to facilitate a smooth emergence from anaesthesia. If necessary, and if not in place from the start, the intraoral detachable plate can be placed back on the multipurpose airway device and the multipurpose airway device can be connected to the anaesthetic circuit and so allow 100% oxygen to be administered to the patient along with gentle positive pressure ventilation. The multipurpose airway according to the invention reduces the risk of coughing and bucking during awakening from surgery which can be very important, for example, in head and neck, plastic surgery, etc. This is due to the fact that, unlike either an ETT or LMA, the multipurpose oropharyngeal airway device does not go into the patient as far and is thus less stimulating to a patient's gag reflex than an ETT or LMA. The multipurpose oral airway device will not stimulate a patient's gag reflex at all.

Although uncommon, patients can unexpectedly bite down hard when emerging from anaesthesia. This can result in dental damage, hypoxia, negative pressure pulmonary oedema, etc. When mounted on an ETT or when placed alongside an LMA or ETT, the proximal end of the substantially straight middle section of the airway body of the multipurpose airway device according to the invention acts as a bite block, preserving the lumen of the ETT and preventing airway obstruction which can lead to hypoxia or rarely negative pressure pulmonary oedema if the patient bites down and blocks the ETT.

As the multipurpose airway device can connect to an anaesthetic or breathing circuit, it can facilitate the easier achievement of positive pressure ventilation than conventional apparatus. This easier positive pressure ventilation is further facilitated by the detachable self retaining and self sealing plate between a patient's lips/cheeks and teeth or gums and pinching or clipping the nose.

Currently, using prior art devices, an anaesthetist has to achieve a seal between a face mask and the patient's face at induction of anaesthesia. If the anaesthetist cannot achieve a seal, the patient may become hypoxic and the anaesthetist will have to rush induction. However, with the detachable intraoral self retaining and self sealing plate and airway body according to the invention in place, a seal is achieved in the patient's mouth, e.g. the patient's between lips/cheeks and teeth or gums. On pinching or clipping the nose, the anaesthetic circuit can then be connected directly to the multipurpose airway device.

Direct connection of the multipurpose airway device to a breathing or anaesthetic circuit is facilitated by the connector. For example, the multipurpose airway device according to the invention can be directly connected to an anaesthetic or breathing circuit. In the event that difficult bag mask valve ventilation is anticipated, the oral multipurpose airway device with the detachable intraoral self retaining and self sealing plate can be positioned before general anaesthetic induction or the multipurpose airway device and plate can be positioned after general anaesthetic induction.

Due to the presence of the central channel in the airway body, the multipurpose airway device can serve as a conduit through which to administer oxygen and inhalational anesthetic agents, e.g. sevoflurane, isoflurane, desflurane, nitrous oxide and the like and mixtures thereof.

The multipurpose airway device can be positioned with or without the detachable self retaining and self sealing plate in an awake patient who has had his airway anaesthetised with local anaesthetic. When the multipurpose airway and plate are used, a breathing or anaesthetic circuit with a proprietary catheter mount adaptor incorporating a self-sealing aperture can be connected to the multipurpose airway device. This facilitates oral fibreoptic intubation while maintaining oxygenation. FOI can be achieved using a proprietary airway exchange catheter (e.g. Aintree airway exchange catheter, Cook Medical airway exchange catheter).

BMV ventilation can be difficult to achieve in the collapsed non-breathing patient even for experienced health care professionals because one has to simultaneously maintain a patent airway while at the same time achieve a seal between the face mask and the patient's face. The multipurpose airway device according to the invention offers an alternative bag valve airway ventilation or mouth valve airway ventilation which many resuscitators will find easier to achieve adequate ventilation. It is much easier to achieve a seal with the multipurpose airway device according to the invention than with a bag mask valve. This is due to the detachable self retaining and self sealing plate which, in use, is placed between lips and cheeks and gums or teeth of a patient. Simultaneously the multipurpose airway device aids in the maintenance of a patent airway. During cardiopulmonary resuscitation, and especially sole provider delivered CPR, delays are minimized between cycles of chest compressions and rescue breaths because the multipurpose airway is retained in the correct position ("hands free").

Due to the fact that the multipurpose oral airway device according to the invention can be placed when the patient is awake or lightly anaesthetised and that the multipurpose oropharyngeal airway device according to the invention can be placed when the patient is lightly anaesthetised (similar to a Guedel airway), an unhurried gentle induction of anaesthesia can be achieved even in those patients where a seal cannot be achieved between mask and face, e.g. patients with facial hair, edentulous, skin condition, facial deformity and obese patients. Simultaneously the multipurpose airway device helps in keeping the patient's airway patent.

The multipurpose airway device according to the invention allows the anaesthetist to achieve an airtight seal as the patient travels from a light to a deeper level of anaesthesia without activating the gag reflex. To avoid stimulating a patient's gag reflex, the multipurpose oral airway device can be used or alternatively the multipurpose oropharyngeal airway device need not be fully advanced into the pharynx until after anaesthesia deepens.

The multipurpose airway when used with a simple chin prop offers an alternative "hands free" airway for general anaesthesia for minor procedures with a spontaneously breathing patient. Apnoea will occur less frequently. However should positive pressure breaths be required the anaesthetist can temporarily pinch the nostrils closed. For those patients where this fails to provide a "hands free" airway a "hands free" airway can be achieved by passing a hypopharyngeal tube through the multipurpose airway device past the epiglottis into the hypopharynx.

During general anaesthesia in the spontaneously breathing patient a closed breathing circuit is simply achieved by sealing the nostrils with a small strip of sticking tape and or by closing the nostrils with a proprietary nose clip such as commonly used by swimmers. In spontaneously breathing patient's inspiration is active and tends to suck the sticking tape and so seals the nostrils; gas entry is via the airway in the mouth. Expiration is passive and gas follows the line of least resistance out the mouth through the multipurpose airway.

The multipurpose airway device according to the invention helps to maintain oxygenation and anaesthesia and can aid oral and nasal FOI. This will be of particular value to the anaesthetist when faced with the unexpected "Difficult Intubation" after induction of anaesthesia. If unexpected difficult intubation occurs both oxygenation and ventilation can be maintained and FOI achieved with, the multipurpose airway device. However, ancillary equipment such as a catheter mount adaptor with a self sealing aperture and airway exchange catheter will be required.

The multipurpose airway device according to the invention can be used as a training tool for FOI. FOI is a core skill for anaesthetists and is often considered the best option for the patient with a difficult airway. Many anaesthetists lack confidence in their ability to perform FOI. Using the multipurpose airway device for FOI makes the procedure less time critical and thus facilitates successful intubation. The breathing or anaesthetic circuit remains connected to the patient during FOI under anaesthesia thus maintaining oxygenation and anaesthesia. During awake FOI the multipurpose airway device can deliver 100% oxygen. Unlike conventional FOI airways (Berman, Ovassapian) when the multipurpose airway device is used, a closed anaesthetic circuit can be used allowing for 100% oxygen and positive pressure breaths to be administered to the patient. A FOB with an airway exchange catheter mounted on it can be passed into the trachea through a proprietary catheter mount adaptor incorporating a self-sealing aperture and then through the multipurpose airway device to the invention. This will allow the patient to be given 100% oxygen and/or his ventilation can be assisted. This makes the procedure of FOI less time critical and so safer.

The multipurpose airway device according to the invention is for use in both anaesthesia of short duration such as required for cardioversion, ECT and minor surgery, as well as in deep sedation such as required for endoscopy, bronchoscopy, colonoscopy and the like. The multipurpose airway device can be used by all airway management personnel, for example, experienced anaesthetists, trainee/junior anaesthetists, Accident and Emergency (A&E, casualty) medical staff, nurses, paramedics and first responders.

From another aspect, the invention provides a means for reversibly locking an ETT to the multipurpose airway by means of a locking device which is attached to the connector of the multipurpose airway device via a push-twist connection. All connections between airway devices and circuits and between parts of circuits are made by "push and twist" actions. For example, to connect a LMA or ETT to the breathing circuit you push the end connector of the ETT into the catheter mount and give it a twist. The locking device comprises a hollow cylinder for insertion into the connector and a finger extending from the cylinder and having a slot to which an ETT may be lashed with a tie or taped. When the locking device is inserted into the connector, only the finger with the slot protrudes from the connector.

By mounting the multipurpose airway device on the ETT in this way the following additional benefits arise:

The integral bite block of the multipurpose airway device protects the lumen of the ETT The patient can more safely undergo a "Deep Extubation" because with the detachable intraoral plate in place (and pinching the nose, if needed), positive pressure breaths of 100% oxygen can be delivered to the patient after extubation.

As explained in Miller's Anesthesia, 7$^{th}$ Edition, 2009, Chapter 50, Extubation may be performed at different depths of anesthesia, with the terms 'awake,' 'light,' and 'deep' often being used. 'Light' implies recovery of protective respiratory reflexes and 'deep' implies their absence. 'Awake' implies appropriate response to verbal stimuli. 'Deep' extubation is performed to avoid adverse reflexes caused by the presence of the tracheal tube and its removal, at the price of a higher risk of hypoventilation and upper airway obstruction. Straining, which could disrupt the surgical repair, is less likely with 'deep' extubation. Upper airway obstruction and hypoventilation are less likely during 'light' extubation, at the price of adverse hemodynamic and respiratory reflexes.

When an anaesthetist intubates a patient he or she usually secures the ETT in one of two ways—by taping the ETT to the patient's face by using strong adhesive tape which sticks to the ETT and to the patient's face or by tying the ETT in place after first passing the tie around the patient's neck. However, the multipurpose airway device and locking mechanism according to the invention are adapted to be mounted on an ETT prior to intubation. The multipurpose airway device and locking mechanism are adapted to be secured to the patient with adhesive tape or by using a tie around the patient's neck. An ETT is secured to the finger of the locking device described herein. This allows for easy intraoperative manipulation of the ETT and avoids the need to remove and reapply any tape to the patient's face, thus making it easier on the patient's skin. In addition, securing the ETT in this way eliminates the risk of kinking the ETT.

Sometimes, the position of an ETT has to be changed intra-operatively. For example, if the ETT has inadvertently been passed too far and beyond the carina (endobronchial intubation). With the prior art devices anaesthetists have to undo the tape and/or tie used to secure the ETT to the patient. If tape has been used this can be hard on the patient's skin. Additionally, in some surgeries the anaesthetist has limited access to the patient because of the presence of sterile drapes. When double lumen tubes are used, as in thoracic surgery, not only does the anaesthetist have to frequently change the position of the tube but also the patient is in the lateral position and it is difficult to undo the tape and/or tie.

In the event the ETT needs to be repositioned when using the multipurpose airway device according to the invention, the tape or tie securing the ETT to the locking device is easily opened and then reapplied after the repositioning. This is especially useful when a double lumen ETT is used, as such double lumen ETTs frequently require repositioning during surgery.

When an ETT is tied in position the knot around the ETT can slip because the wall of the ETT is smooth; because of this the ETT may advance further into the patient into an endobronchial position or alternatively slip out leading to accidental extubation. When the ETT is secured to the finger of the locking device and the multipurpose airway device is tied to the patient the knot is secure in the groove of the multipurpose airway device and doesn't slip.

From a further aspect the invention provides a method for creating an airtight seal for an ETT such method involves using the self retaining and self sealing plate described herein to seal the mouth. Nasal occluding clips are required to seal the nose. A cuffed endotracheal tube is most commonly used for positive pressure ventilation, with an airtight seal created by inflating the cuff in the trachea. In some circumstances, the inflated cuff can cause ischaemic damage to the trachea either because the cuff has had to be inflated to too high a pressure in order to achieve an airtight seal and or the patient has been haemodynamically unstable and hypotensive and so at greater risk of ischaemic damage to his trachea. For the same reason uncuffed endotracheal tubes are often preferred in children. When the self retaining and self sealing plate is used in combination with an ETT whose pilot balloon tube emerges from close to the proximal end of the shaft of the ETT it offers an alternative sealing mechanism for positive pressure ventilation. The cuff of the ETT could be intermittently deflated in patients at high risk of such ischaemic damage in order to temporarily increase blood flow to the tracheal mucosa. Additionally the cuff on an ETT may malfunction and deflate or during airway surgery be punctured by a surgical blade or needle.

Thus, viewed from a further aspect, the invention provides a multipurpose airway pack comprising: a multipurpose oral or oropharyngeal airway device as described herein, a self retaining and self sealing intraoral plate, an ETT locking device as described herein; and optionally a tie for attaching the device to a patient's face, for example an elasticated cloth tie, preferably 1 m in length.

From a further aspect, the invention provides a method of using the oral airway device described herein to facilitate preoxygenation prior to anaesthetisation of a mask phobic patient, said method comprising the following steps:
(i) Place the distal end of the oral airway device in the mouth of the patient until the intraoral seal reaches the gums and close the patient's mouth over the intraoral seal;
(ii) Connect the proximal end of the oral airway device to a breathing or anaesthetic circuit delivering 100% oxygen via the connector on the airway body; and
(iii) Either clip or pinch the patient's nose or request the patient to pinch his own nostrils closed and to breathe through his mouth.

This method is especially useful for claustrophobic patients who refuse to breathe from a face mask. Anaesthetists routinely preoxygenate patients, especially in emergency cases before anaesthesia.

From yet a further aspect, the invention provides a method of using the oral airway device described herein to facilitate enhanced medical care of an intubated patient, said method comprising the following steps:
(i) Attach the ETT locking device described herein to the connector on the airway body;
(ii) Attach the detachable intraoral plate into the groove on the connector of the oral airway device;
(iii) Mount the oral airway device with the intraoral plate and locking device attached onto the endotracheal tube and slide the oral airway device to the proximal end of the endotracheal tube prior to intubation;
(iv) Intubate the patient;
(v) Slide the oral airway device and locking device along the endotracheal tube until the straight portion of the airway body is situated between the patient's top and bottom teeth or gums if edentulous;
(vi) Position the intraoral plate of the oral airway device outside the patient's lips with it's long axis facing head to toe to avoid blocking the mouth;
(vii) Tape or tie the endotracheal tube to the finger of the locking device; and
(viii) Tape the oral airway device to the face of the patient or tie the oral airway after first looping the tie around the patient's neck.

By sliding the oral airway device to the proximal end of the endotracheal tube prior to intubation, the oral airway device can act as a bite block. The intraoral plate positioned outside the patient's lips in step (vi) functions as a cushion when the airway body is tied to the patient.

Deep extubation is generally performed to avoid adverse reflexes caused by the presence of the tracheal tube and its removal, at the price of a higher risk of hypoventilation and upper airway obstruction. In deep extubation, the endotracheal tube is removed from the patient when the patient is still anaesthetized and before the airway reflexes have returned. The ETT is secured with the locking device and "Deep Extubation" or safer "Deep Extubation" is facilitated with the above method as the ETT and locking device are removed before the return of the airway reflexes, the anaesthetic or breathing circuit is connected to the oral airway device and the intraoral plate is positioned between the patient's lips and teeth or gums.

From yet a further aspect, the invention provides a method of using the oral multipurpose airway device described herein for deep extubation of a patient, said method comprising the following steps:
(i) Attach the ETT locking device described herein to the connector on the airway body;
(ii) Mount the oral airway device with the intraoral plate and locking device attached onto the endotracheal tube and slide the oral airway device to the proximal end of the endotracheal tube prior to intubation;
(iii) Intubate the patient;
(iv) Slide the oral airway device and locking device back down the endotracheal tube so that the body of the airway is situated between the top and bottom teeth or gums if edentulous;
(v) Tape or tie the endotracheal tube to the finger of the locking device;
(vi) Tape the oral airway to the patient's face or tie the oral airway after first looping the tie around the patient's neck;
(vii) At the time of extubation, position the intraoral plate of the oral airway device between the patient's gums or teeth and lips;
(viii) When ready extubate the patient by pulling the endotracheal tube and locking device out of the patient and out of the oral airway.

Further optional steps include: Suctioning prior to inserting the plate between the lips and cheeks and the gums and teeth; and optionally connecting an anaesthetic or breathing circuit to the distal end of the oral airway device to administer positive pressure breathing.

From yet a further aspect, the invention provides a method of using the self retaining and self sealing plate described herein for smooth and or deep extubation of a patient when an ETT is used alone without the oral multipurpose airway device, said method comprising the following steps:
(i) Mount the plate onto an ETT whose pilot balloon tube exits the ETT close to it's proximal end and push the plate to the proximal end of the ETT;
(ii) Intubate the patient;
(iii) Tape the ETT to the patient's face or tie the ETT after first looping the tie around the patient's neck;
(iv) At the time of extubation, position the intraoral plate between the patient's gums or teeth and lips;
(v) When ready extubate the patient by pulling the endotracheal tube out of the trachea and larynx and leave the distal end in the pharynx;
(vi) The ETT can now be used as an oropharyngeal airway or withdrawn further and used as an oral airway.

Further optional steps include: Suctioning prior to inserting the plate between the lips and cheeks and the gums and teeth; and optionally connecting an anaesthetic or breathing circuit to the distal end of the ETT to administer positive pressure breathing.

The invention further provides a method of using the self retaining and self sealing plate described herein to facilitate positive pressure breathing when an LMA is used either because the cuff on the LMA has failed to seal the LMA or the Anaesthetist has chosen not to inflate the cuff to reduce the risk of a sore throat, said method comprising the following steps:

(i) Mount the plate onto a specially adapted LMA whose pilot balloon tube exits from the proximal end of the LMA, from the proximal end;
(ii) Insert the LMA into the patient;
(iii) Position the intraoral plate between the patient's gums or teeth and lips;
(iv) Tape the LMA to the patient's face or tie the LMA after first looping the tie around the patient's neck;
(v) Apply nasal occluding device for positive pressure breaths;
(vi) When ready remove the LMA.

The invention further provides a method of using the oropharyngeal airway device described herein to facilitate positive pressure breathing during resuscitation of an unconscious patient, said method comprising the following steps:
(i) Fit the detachable intraoral plate onto the groove in the connector on the airway body;
(ii) Place the distal end of the oropharyngeal airway body into the patient's oropharynx via the patient's mouth;
(iii) Connect the proximal end of the oropharyngeal airway device to a breathing or anaesthetic circuit via the connector on the airway body or alternatively to the one way fluid filter for mouth to airway positive pressure breaths; and
(iv) Clip or pinch the patient's nose to close the patient's nostrils.

From yet a further aspect, the invention provides a method of using the oropharyngeal airway device described herein for fibreoptic intubation of an anaesthetised patient:
(i) Fit the detachable intraoral plate into the groove on the connector on the airway body;
(ii) Place the oropharyngeal airway device into the patient's oropharynx via the patient's mouth;
(iii) Connect an anaesthetic circuit to the connector of the oropharyngeal airway device;
(iv) Pinch or clip the patient's nostrils;
(v) Mount a proprietary airway exchange catheter (e.g. an Aintree or Cook medical proprietary airway exchange catheter) onto the fibreoptic bronchoscope;
(vi) Pass the bronchoscope through a proprietary airway connector with a self-sealing aperture through the oropharyngeal airway device into the patient's larynx and trachea;
(vii) Advance the airway exchange catheter over the bronchoscope into the trachea;
(viii) Remove the bronchoscope;
(ix) Temporarily disconnect the anaesthetic circuit from the oropharyngeal airway device and railroad an endotracheal tube over the airway exchange catheter into the trachea;
(x) Remove the airway exchange catheter and connect the anaesthetic circuit to the endotracheal tube.

The oropharyngeal airway device described herein may also be used for fibreoptic intubation of an awake patient.

BRIEF DESCRIPTION OF THE DRAWINGS

The invention will now be described with reference to the accompanying drawings which show embodiments of the multipurpose airway device according to the invention in which:—

FIG. 1b is another perspective view of the multipurpose oral airway device of FIG. 1a;

FIG. 5b is another perspective view of the multipurpose oral airway device of FIG. 5a;

FIGS. 7a and 7b are end on views of the multipurpose oral airway device of FIG. 5a viewed from the proximal and distal end, respectively;

FIG. 8 is a perspective view of a preferred detachable intraoral seal;

FIG. 10 is a plan view of the multipurpose airway device of FIG. 9b;

FIG. 11 is a side view of the multipurpose airway device of FIG. 9b;

FIGS. 14a, 14b and 14c are, respectively, perspective, side and plan views of a multipurpose oropharyngeal airway device according to the invention suitable for a child with the intraoral seal detached;

FIGS. 15a and 15b are perspective views of the multipurpose oropharyngeal airway device of FIG. 14a with the intraoral seal attached.

FIGS. 17, 18 and 19 are respectively a side view, plan view and perspective view of a fifth embodiment of a multipurpose oral airway device and intraoral seal according to the invention and which is suitable for an adult;

FIGS. 36, 37 and 38 are an end view, cross-sectional side and cross-sectional side view of the fifth embodiment modified by an included tube;

DETAILED DESCRIPTION OF THE PREFERRED EMBODIMENT(S)

Figure 1A:
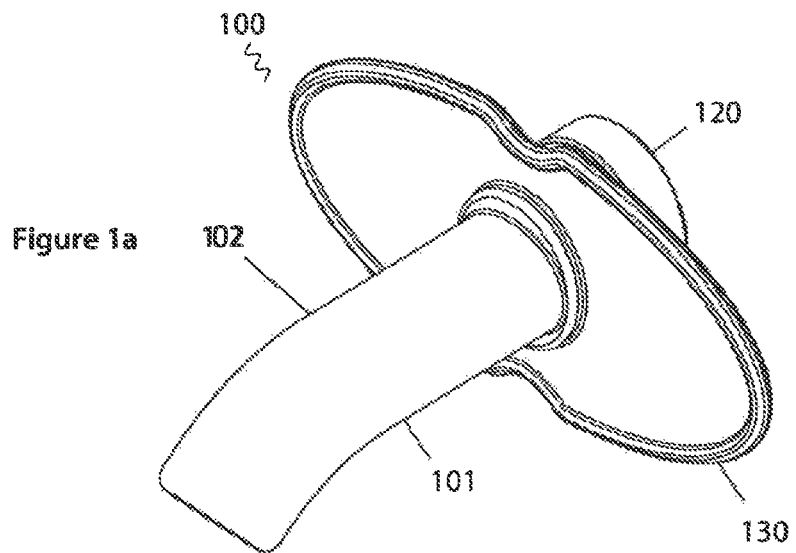
FIG. 1a is a perspective view of a preferred multipurpose oral airway device according to the invention suitable for an adult.
Figure 1B:
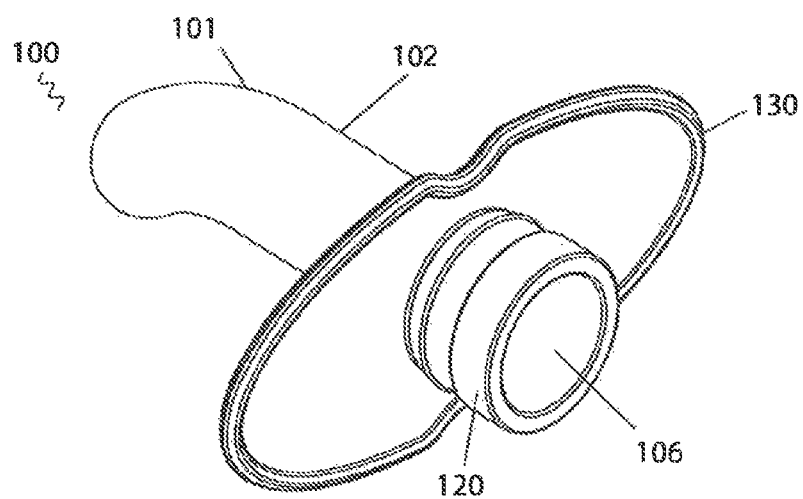
Figure 4:
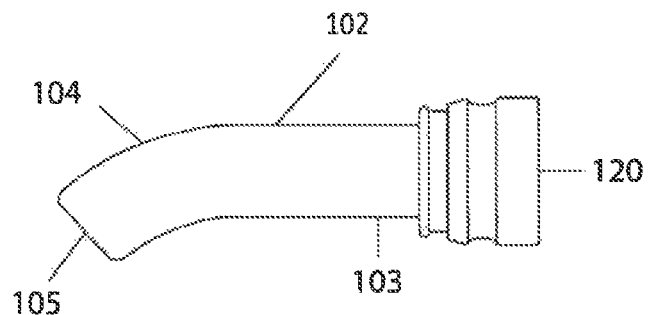
FIG. 4 is a side view of FIG. 2.
Figure 3:
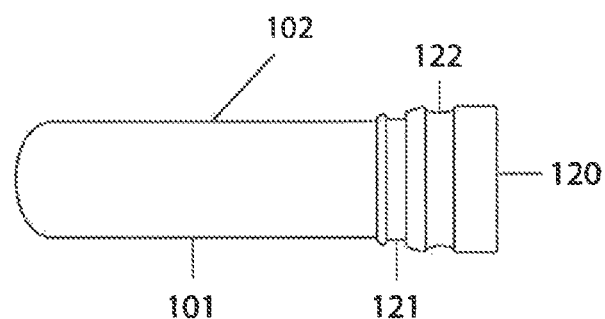
FIG. 3 is a plan view of FIG. 2.
Figure 2:
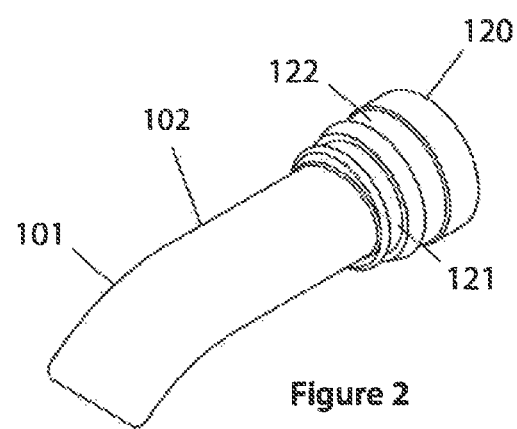
FIG. 2 is a perspective view of the multipurpose oral airway device of FIGS. 1a and 1b with the intraoral seal detached.
Figure 5A:
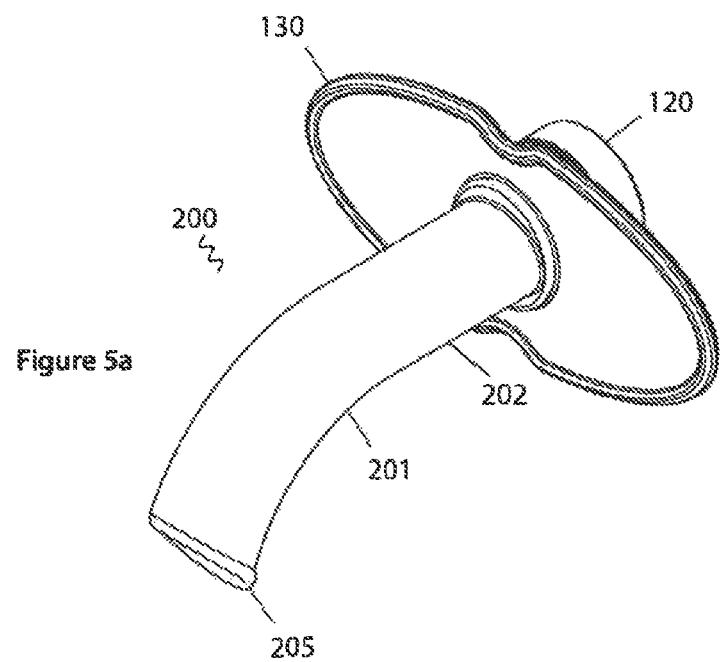
FIG. 5a is a perspective view of a preferred multipurpose oropharyngeal airway device according to the invention suitable for an adult.
Figure 5B:
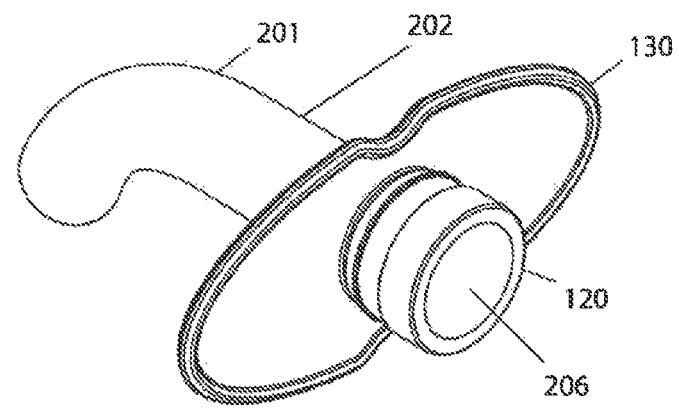
Figure 6B:
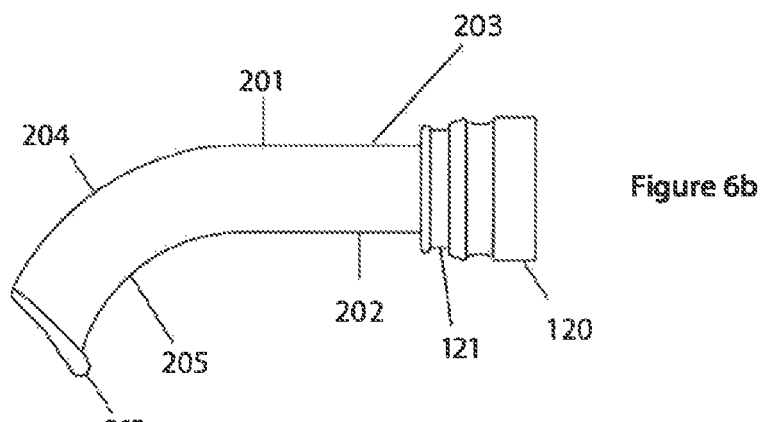
FIGS. 6a, 6b and 6c are, respectively, perspective, side and plan views of the multipurpose airway device of FIGS. 5a and 5b with the intraoral seal detached.
Figure 6C:
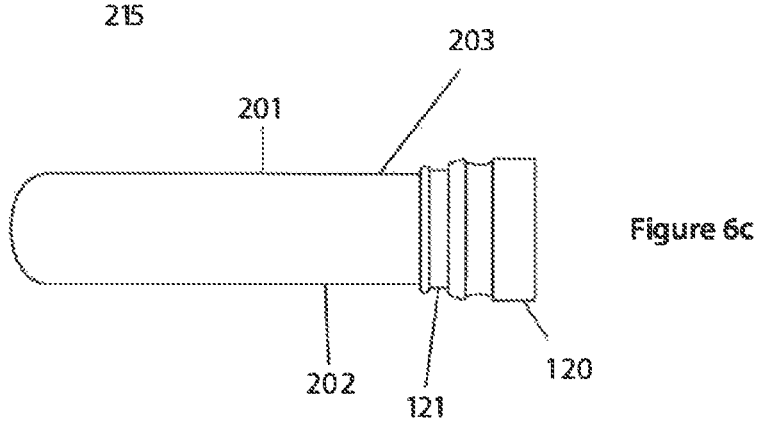
Figure 6A:
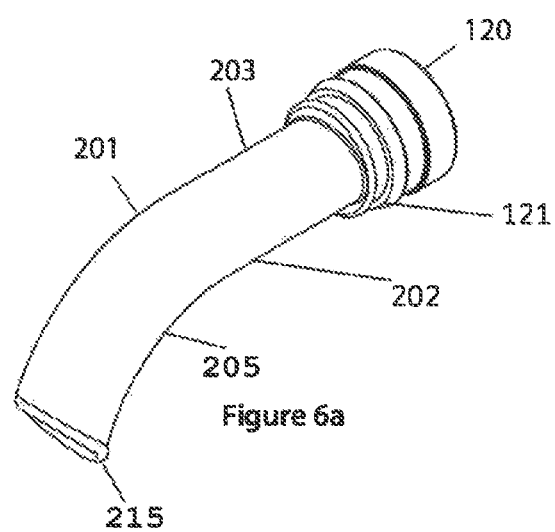

Referring to the Figures, like reference numerals refer to like features. In FIGS. 1 to 4 a multipurpose airway device according to one embodiment of the present invention is shown, generally indicated by the reference numeral 100. Multipurpose airway device 100 is an oral airway device suitable for an adult and comprises an elongate, tubular airway body 101. Airway body 101 has a substantially straight section 102, the proximal end of which is adapted to function as an integral bite block 103, a curved distal section 104 with a distal tip 105 and a central channel 106 for accepting an intubation device (not shown). Distal tip 105 and curved distal section 104 facilitate placement of the airway device 100 into a patient's mouth.

Oral airway device 100 also has a substantially oval, infinity symbol-shaped detachable intraoral seal 130 having a central aperture 131 for receiving the airway body 101. Central aperture 131 is substantially circular and located centrally with respect to each of the minor and major axes of the intraoral seal 130 and provides a passage through the intraoral seal 130. Detachable intraoral seal 130 is made of flexible material and is adapted to fit between a patient's gums and lips to seal the patient's mouth opening. The infinity or butterfly shape reduces or prevents the seal 130 from irritating frenula between the lips and gums of the patient. A connector 120 for facilitating attachment of anaesthesia equipment is attached to the proximal end of airway body 101 and has a groove 121 for accepting detachable intraoral seal 130 and a groove 122 for accepting tie material for attaching the airway device to a patient. Airway body 101 is adapted to pass through central aperture 131 of the detachable intraoral seal 130 until the seal is located in groove 121 of connector 120.

The underside of the substantially straight section 102 of airway body 101 is provided with a glottal surface which has a horizontal profile when in use it is in relative position with the tongue and which sweeps down substantially following the contours of the mouth to increase its area of contact with the tongue. Distal tip 105 has a curved underside which aids placement of oral airway device 100 into the patient's mouth by spreading pressure across the tongue. Multipurpose oral airway device 100 can thus be placed into the patient without turning it upside down first.

Detachable intraoral seal 130 is placed with or independently of multipurpose airway device 100 either before or after induction of anaesthesia. For example, multipurpose airway device 100 is passed through aperture 131 of intraoral seal 130 after the induction of anaesthesia. Alternatively, multipurpose airway device 100 together with the intraoral seal attached is positioned before induction of anaesthesia.

Oral airway device 100 is used according to the following method: Before the induction of general anesthesia, the distal end of oral airway device 100 is placed in the mouth of the patient and connected to a breathing or anaesthetic circuit via connector 120. After the induction of general anaesthesia the patient's nose is then clipped or pinched to close the nostrils. This allows for positive pressure breathing where a seal would not be achievable between facemask and face.

Referring now to FIGS. 5a to 8, a multipurpose oropharyngeal airway device according to one embodiment of the present invention is shown, generally indicated by the reference numeral 200. Multipurpose airway device 200 is suitable for an adult and comprises an elongate, tubular airway body 201. Airway body 201 has a substantially straight section 202, the proximal end of which is adapted to function as an integral bite block 203, a curved distal section 204 with a distal tip 205 and a central channel 206 for accepting an intubation device (not shown). Distal tip 205 and curved distal section 204 facilitate placement of the airway device 200 into a patient's mouth and throat.

Oropharyngeal airway device 200 also has the substantially oval, butterfly-shaped detachable intraoral seal 130 and connector 120. Airway body 201 is adapted to pass through central aperture 131 of the detachable intraoral seal 130 until the seal is located in groove 121 of connector 120.

The underside of the substantially straight section 202 of airway body 201 is provided with a glottal surface which has a horizontal profile when in use it is in relative position with the tongue and which sweeps down substantially following the contours of the mouth to increase its area of contact with the tongue. This assists in preventing the tongue from obstructing the pharynx. Distal tip 205 has a curved underside which aids placement of oropharyngeal airway device 200 into the patient's mouth and throat by spreading pressure across the back of the tongue. Distal tip 205 is provided with a downwardly offset rim 215 which aids placement of oropharyngeal airway device 200 into the patient's mouth and throat by spreading pressure across the back of the tongue. Multipurpose oropharyngeal airway device 200 can thus be placed into the patient without turning it upside down first.

Detachable intraoral seal 130 is placed with or independently of multipurpose airway device 200 after induction of anaesthesia. For example, multipurpose airway device 200 is passed through aperture 131 of intraoral seal 130 after the induction of anaesthesia. Alternatively, multipurpose airway device 200 together with intraoral seal 130 attached is positioned after induction of anaesthesia. Distal tip 205 can be advanced or withdrawn into or out of the patient's pharynx to allow for multipurpose oropharyngeal airway device 200 to be advanced gradually as the level of anaesthesia deepens without activating the patient's gag reflex.

As shown in FIGS. 9a to 11, an ETT locking device 240 may be attached to connector 120 of multipurpose airway device 200 using a typical push-twist connection. ETT locking device 240 comprises a hollow cylinder 241 for insertion into connector 120 and a finger 242 extending from cylinder 241 and having a slot 243 to which an ETT may be lashed with a tie T or taped, as shown in FIG. 9c. When ETT locking device 240 is inserted into connector 120, only finger 242 with slot 243 protrudes from connector 120.

In use, multipurpose airway device 200 is secured to the patient and an ETT is secured to airway device 200 via ETT locking device 240. This allows for easy intraoperative manipulation of the ETT and avoids the need to remove and reapply any tape to the patient's face, thus making it easier on the patient's skin. In addition, securing the ETT in this way eliminates the risk of kinking the ETT. In the event the ETT needs to be repositioned, the tape or tie T securing the ETT to the finger 242 of ETT locking device 240 is easily opened and then secured again after the repositioning. This is especially useful when a double lumen ETT is used, as such double lumen ETTs frequently require repositioning during surgery.

Figure 9A:
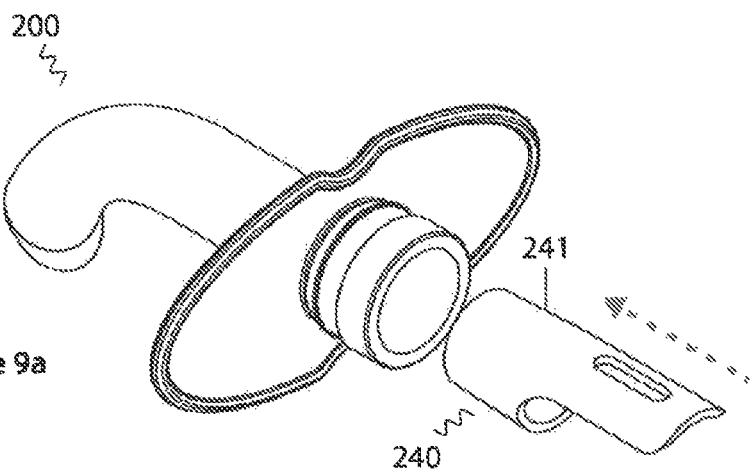
FIGS. 9a and 9b are perspective views of the multipurpose airway device of FIGS. 5a and 5b and a preferred ETT locking device.
Figure 9B:
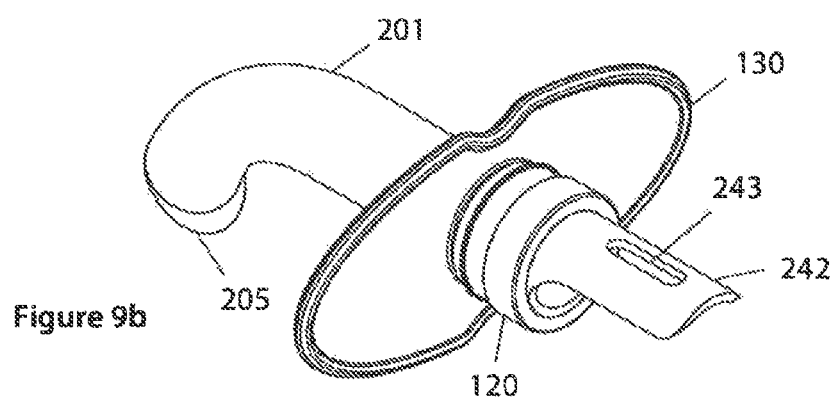
Figure 9C:
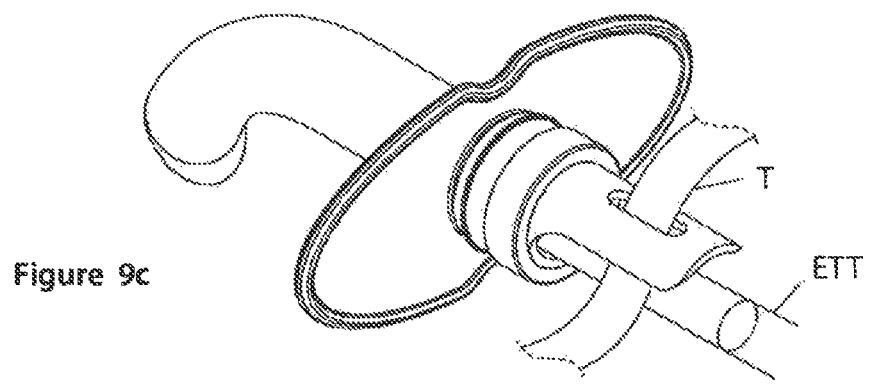
FIG. 9c is a perspective view of FIG. 9b with ETT attached.
Figure 12B:
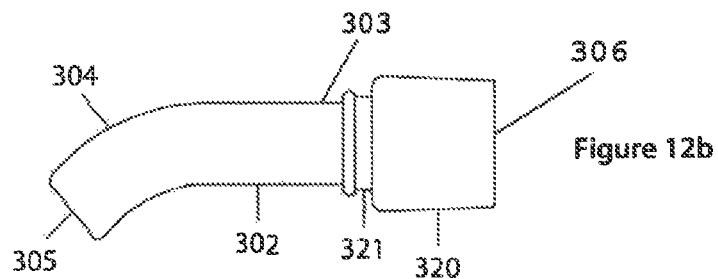
FIGS. 12a, 12b and 12c are, respectively, perspective, side and plan views of a multipurpose oral airway device according to the invention suitable for a child with the intraoral seal detached.
Figure 12C:
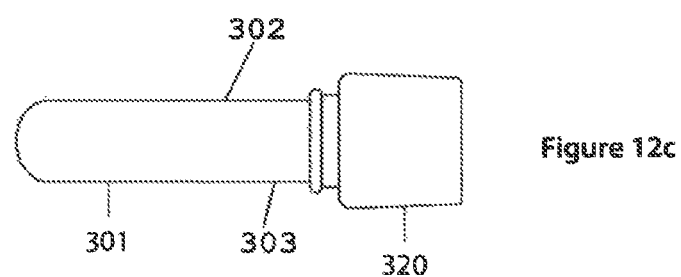
Figure 12A:
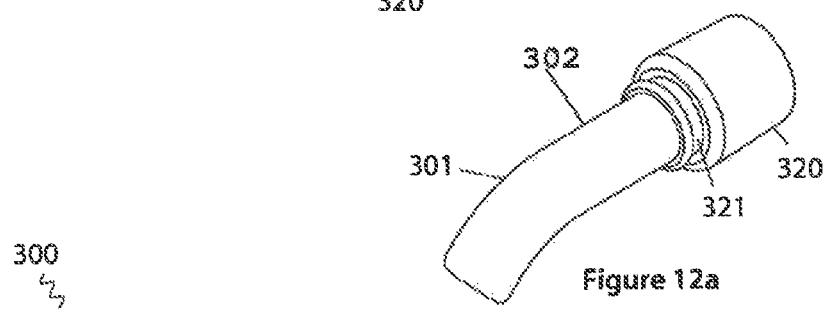
Figure 13A:
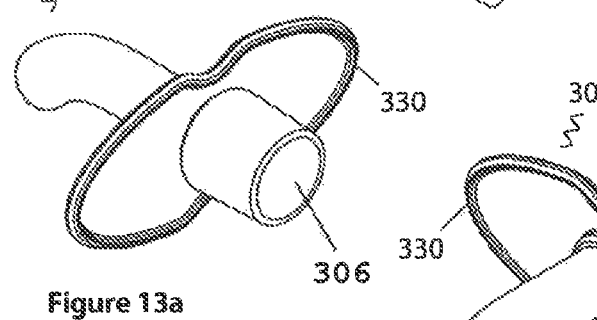
FIGS. 13a and 13b are perspective views of the multipurpose oral airway device of FIG. 12a with the intraoral seal attached.
Figure 13B:
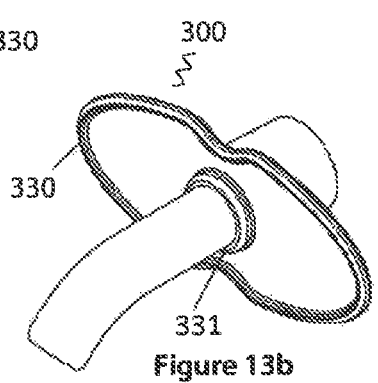
Figure 16A:
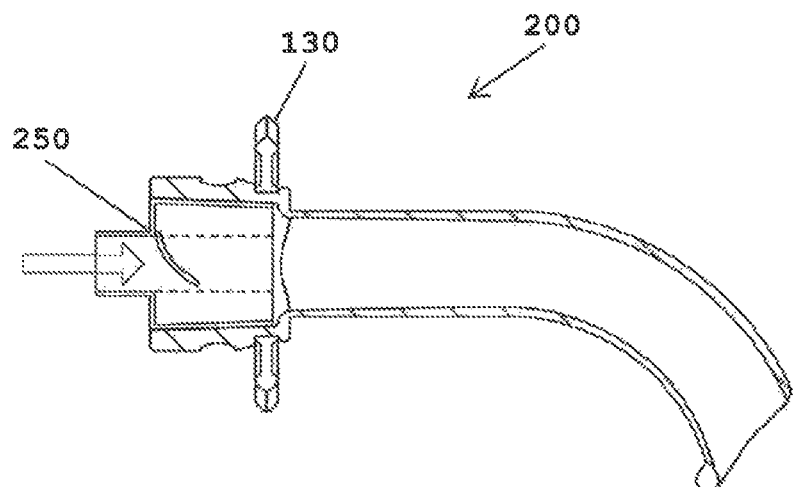
FIGS. 16a and 16b are cross-sectional side views of the multipurpose oropharyngeal device of FIG. 9a with a one-way valve in the connector.
Figure 16B:
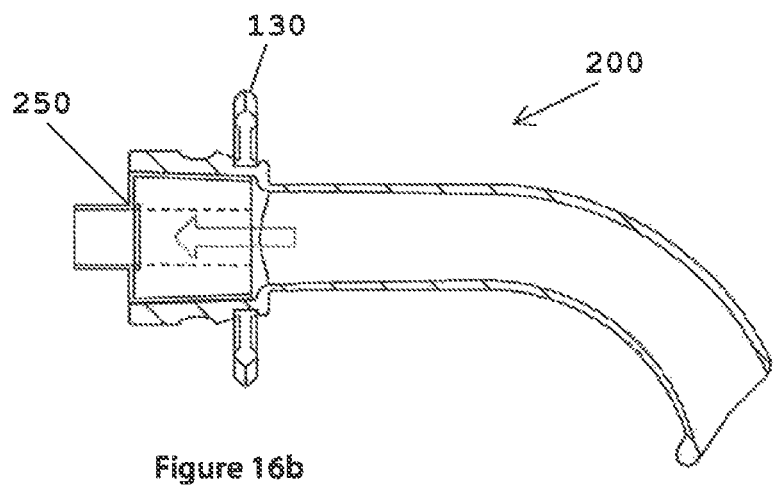
Figure 20:
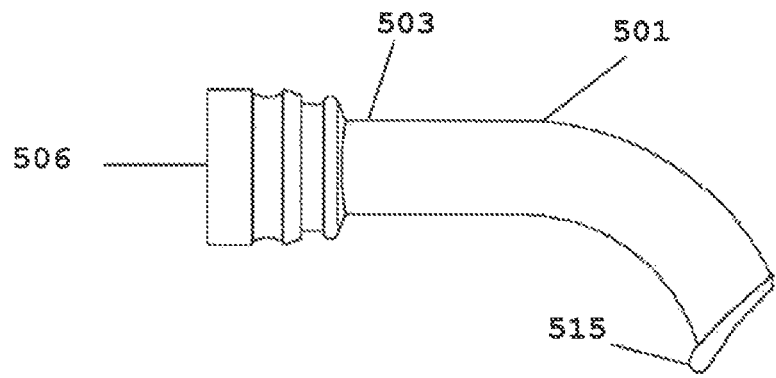
FIGS. 20, 21 and 22 are respectively a side view, plan view and perspective view of the airway device of the embodiment of FIGS. 17 to 19 without the intraoral seal.
Figure 21:
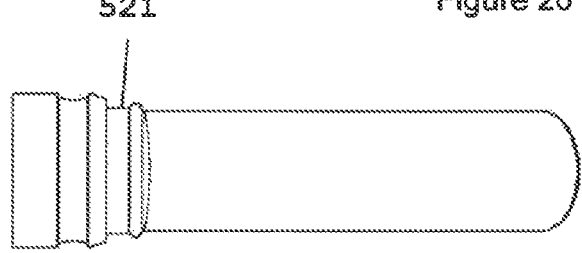
Figure 22:
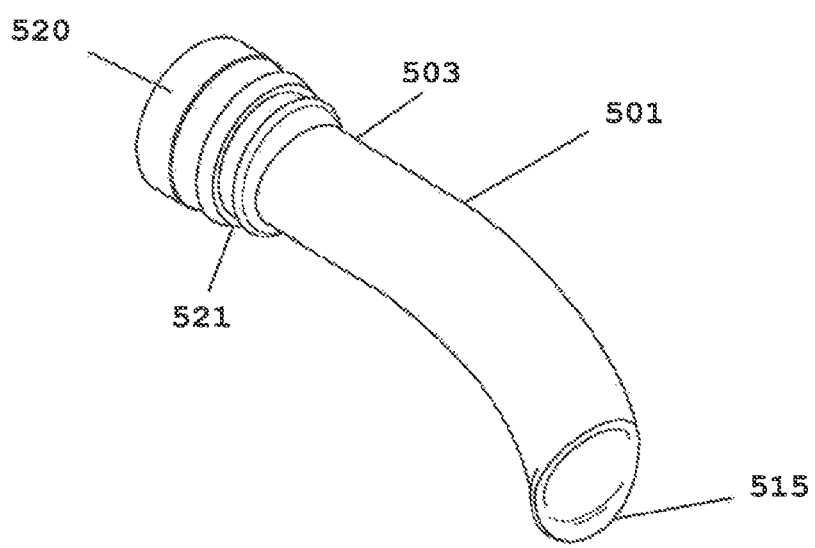
Figure 23:
FIGS. 23, 24 and 25 are respectively three successive perspective views showing the assembly and manipulation of the embodiment of FIGS. 17 to 22.
Figure 24:
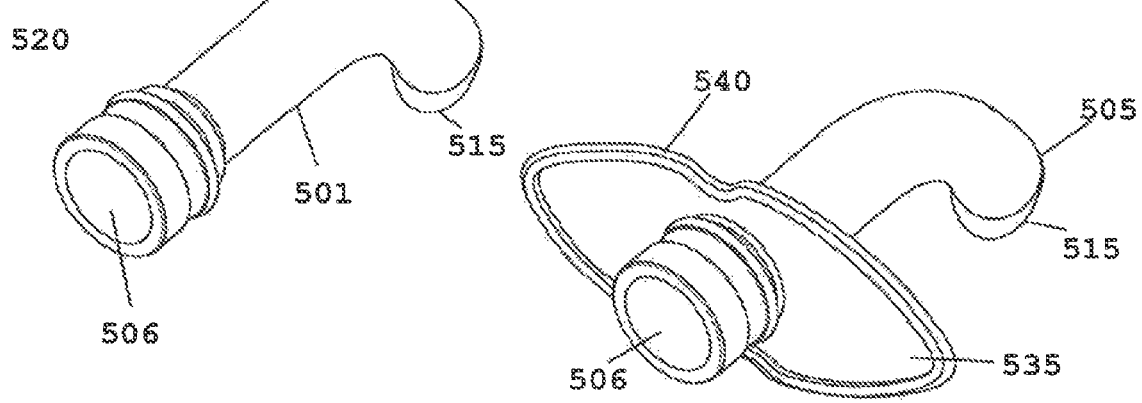

FIGS. 16a and 16b show the multipurpose oropharyngeal device 200 of FIG. 9a with a one-way valve 250 in the connector. The one-way valve 250 is similar to those found on rescue masks used for resuscitation.

Referring now to FIGS. 12a to 13b, a multipurpose oral airway device according to one embodiment of the present invention is shown, generally indicated by the reference numeral 300. Multipurpose airway device 300 is suitable for a child and comprises an elongate, tubular airway body 301. Airway body 301 has a substantially straight section 302, the proximal end of which is adapted to function as an integral bite block 303, a curved distal section 304 with a distal tip 305 and a central channel 306 for accepting an intubation device (not shown). Distal tip 305 and curved distal section 304 facilitate placement of the airway device 300 into a patient's mouth.

Oral airway device 300 also has a substantially oval, infinity symbol-shaped detachable intraoral seal 330 having a central aperture 331 for receiving the airway body 301. Central aperture 331 is substantially circular and located centrally with respect to each of the minor and major axes of the intraoral seal 330 and provides a passage through the intraoral seal 330. Detachable intraoral seal 330 is made of flexible material and is adapted to fit between a patient's gums and lips to seal the patient's mouth opening. The infinity or butterfly shape reduces or prevents the seal 330 from irritating frenula between the lips and gums of the patient. The intraoral 330 seal for a child is similar to the intraoral seal 130 for an adult, as shown in FIGS. 7a, 7b and 8, apart from being a smaller size.

A connector 320 for facilitating attachment of anaesthesia equipment is attached to the proximal end of airway body 301 and has a groove 321 for accepting detachable intraoral seal 330. Airway body 301 is adapted to pass through central aperture 331 of the detachable intraoral seal 330 until the seal is located in groove 321 of connector 320.

The underside of the substantially straight section 302 of airway body 301 is provided with a glottal surface which has a horizontal profile, when in use it is in relative position with the tongue and which sweeps down substantially following the contours of the mouth to increase its area of contact with the tongue.

Child size connector 320 is of a reduced outer diameter compared to adult connector 120 as it is fitted to the breathing circuit as a male connector, whereas the larger diameter adult size connector 120 acts as a female connector when fitting to the breathing circuit.

Referring now to FIGS. 14a to 14c, 15a and 15b a multipurpose oropharyngeal airway device according to one embodiment of the present invention is shown, generally indicated by the reference numeral 400. Multipurpose airway device 400 is suitable for a child and comprises an elongate, tubular airway body 301. Airway body 301 has a substantially straight section 302, the proximal end of which is adapted to function as an integral bite block 303, a curved distal section 304 with a distal tip 305 and a central channel 306 for accepting an intubation device (not shown). Distal tip 305 and curved distal section 304 facilitate placement of the airway device 400 into a patient's mouth and throat.

Oropharyngeal airway device 400 also has a substantially oval, infinity symbol-shaped detachable intraoral seal 330 having a central aperture 331 for receiving the airway body 301. Central aperture 331 is substantially circular and located centrally with respect to each of the minor and major axes of the intraoral seal 330 and provides a passage through the intraoral seal 330. Detachable intraoral seal 330 is made of flexible material and is adapted to fit between a patient's gums and lips to seal the patient's mouth opening. The infinity or butterfly shape reduces or prevents the seal 330 from irritating frenula between the lips and gums of the patient. The intraoral 330 seal for a child is similar to the intraoral seal 130 for an adult, as shown in FIGS. 7a, 7b and 8, apart from being a smaller size.

A connector 320 for facilitating attachment of anaesthesia equipment is attached to the proximal end of airway body 301 and has a groove 321 for accepting detachable intraoral seal 330. Airway body 301 is adapted to pass through central aperture 331 of the detachable intraoral seal 330 until the seal is located in groove 321 of connector 320.

The underside of the substantially straight section 302 of airway body 301 is provided with a glottal surface which has a horizontal profile, when in use it is in relative position with the tongue and which sweeps down substantially following the contours of the mouth to increase its area of contact with the tongue. This assists in preventing the tongue from obstructing the pharynx. Distal tip 305 is provided with a downwardly offset rim 415 which aids placement of oropharyngeal airway device 400 into the patient's mouth and throat by spreading pressure across the back of the tongue. Multipurpose oropharyngeal airway device 400 can thus be placed into the patient without turning it upside down first.

Child size connector 320 is of a reduced outer diameter compared to adult connector 120 as it is fitted to the breathing circuit as a male connector, whereas the larger diameter adult size connector 120 acts as a female connector when fitting to the breathing circuit.

The fifth embodiment of a multipurpose oral airway device and intraoral seal will now be described with reference to FIGS. 17 to 27.

In these drawings, a multipurpose oropharyngeal airway device of the present invention is shown, generally indicated by the reference numeral 500, which is suitable for an adult and includes an elongate, tubular airway body 501. It has a substantially straight section 502, the proximal end of which is adapted to function as an integral bite block 503, a curved distal section 504 with a distal tip 505 and a central channel 506 for accepting an intubation device (not shown). Distal tip 505 and curved distal section 504 facilitate placement of the airway device 500 into a patient's mouth and throat. The distal tip 505 is provided with a downwardly offset rim 515.

Oropharyngeal airway device 500 also has a substantially oval, butterfly-shaped detachable intraoral seal 530 and connector 520. Airway body 501 is adapted to pass through central aperture 531 of the detachable intraoral seal 530 until the seal is located in groove 521 of connector 520. The intraoral seal 530 extends transverse to the longitudinal axis of the tubular airway body 501 and narrows down at both sides to rounded points 535. A rim 540 extends about the perimeter of the seal 530 so as to provide the necessary rigidity and stiffness. Two central concave contours 542 are provided in the rim 540 which aids bending of the seal and location in the patient's mouth.

The underside of the substantially straight section 502 of airway body 501 is provided with a glottal surface which has a horizontal profile when in use it is in relative position with the tongue and which sweeps down substantially following the contours of the mouth to increase its area of contact with the tongue. This assists in preventing the tongue from obstructing the pharynx. Distal tip 505 has a curved underside which aids placement of oropharyngeal airway device 500 into the patient's mouth and throat by spreading pressure across the back of the tongue. Multipurpose oropharyngeal airway device 500 can thus be placed into the patient without turning it upside down first. Also the downwardly extending rim 515 engages with the back of the tongue and ends proximal to the epiglottis (see FIGS. 26 and 27).

Figure 25:
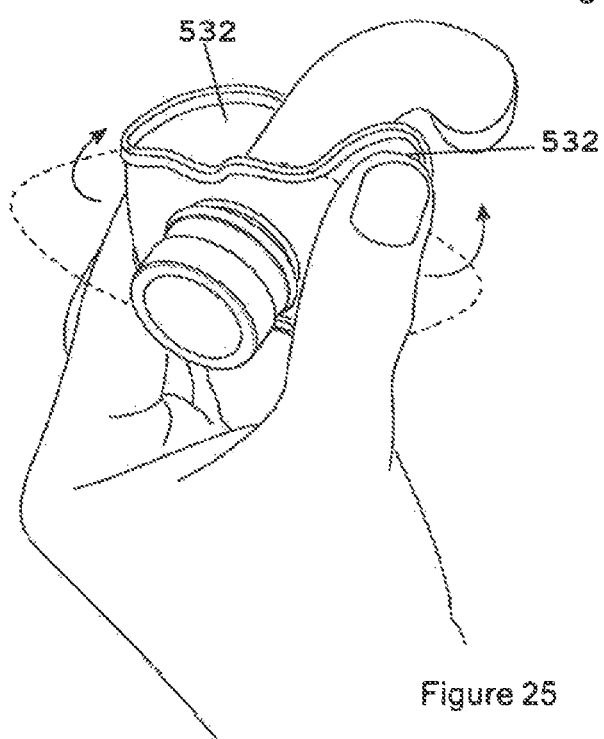
Figure 26:
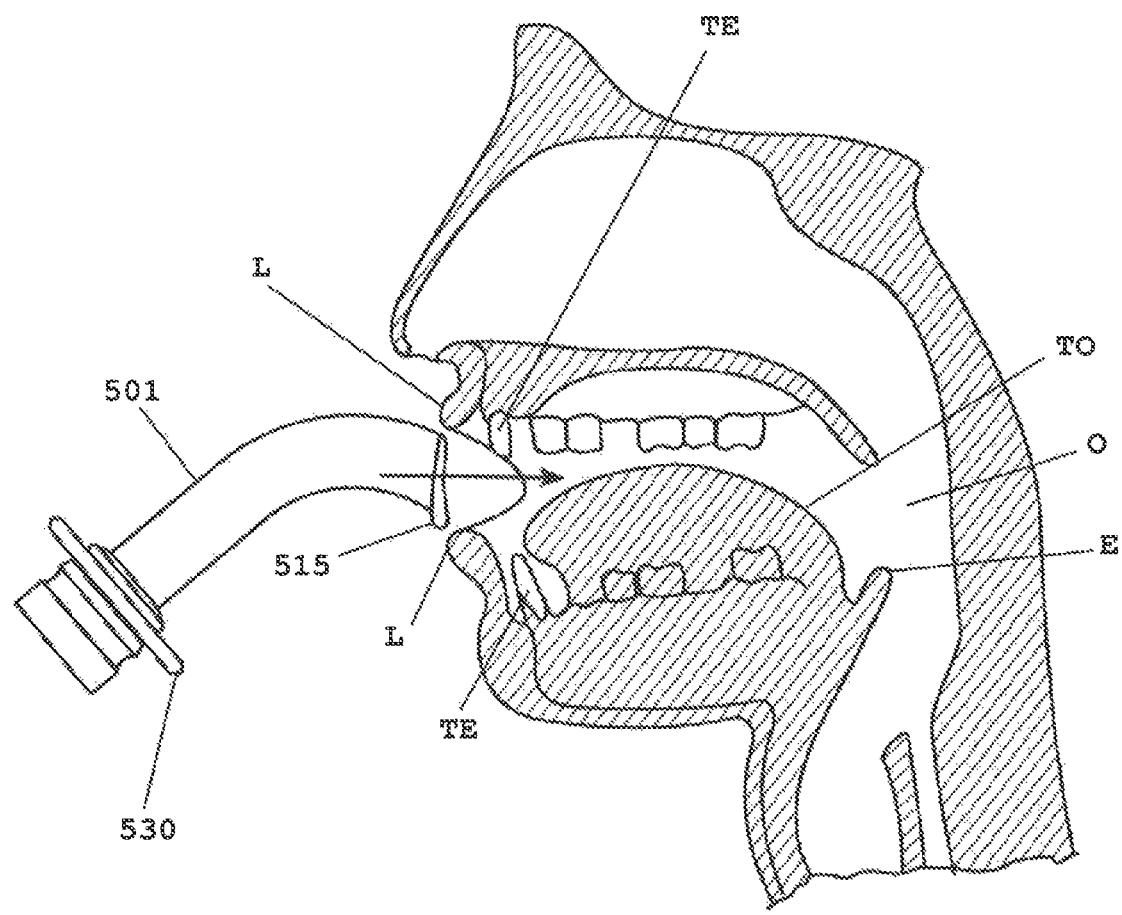
FIG. 26 is a side view illustrating how the embodiment of FIGS. 17 to 25 is inserted into the mouth of a patient.
Figure 27:
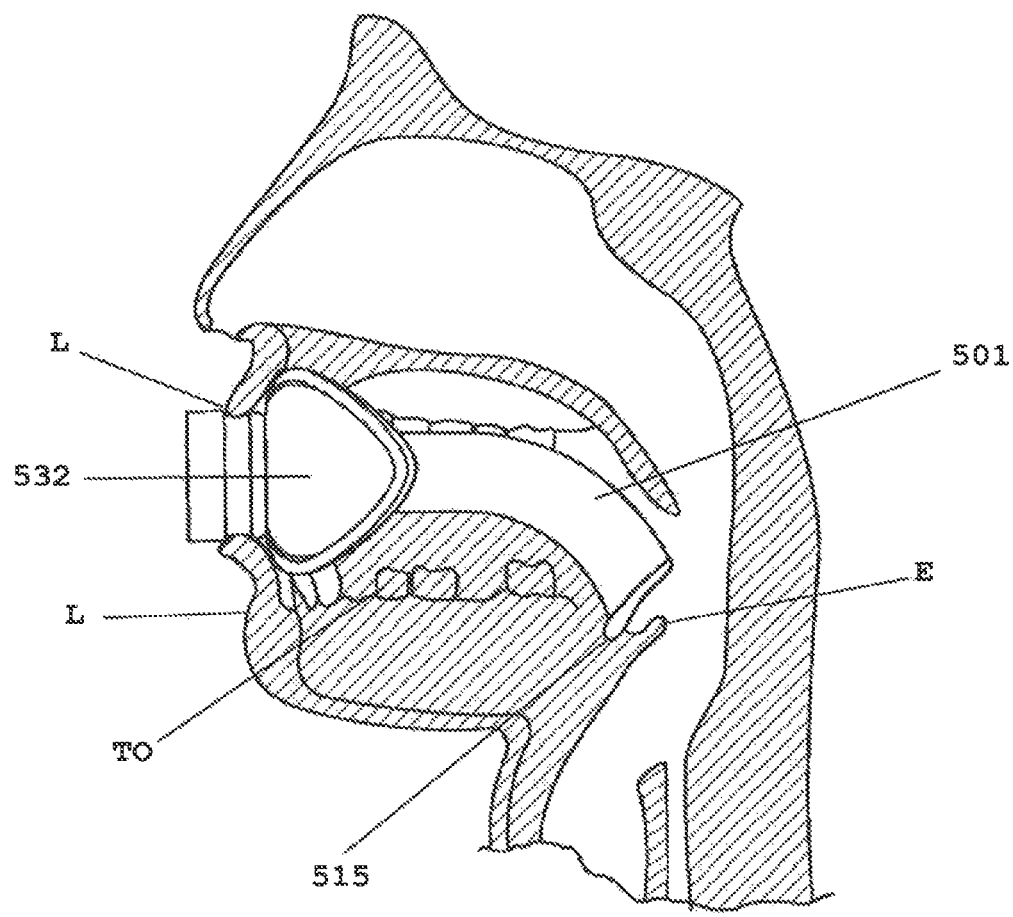
FIG. 27 is a side view of the embodiment of FIGS. 17 to 25 showing how it is located in position in the patient's mouth.
Figure 28:
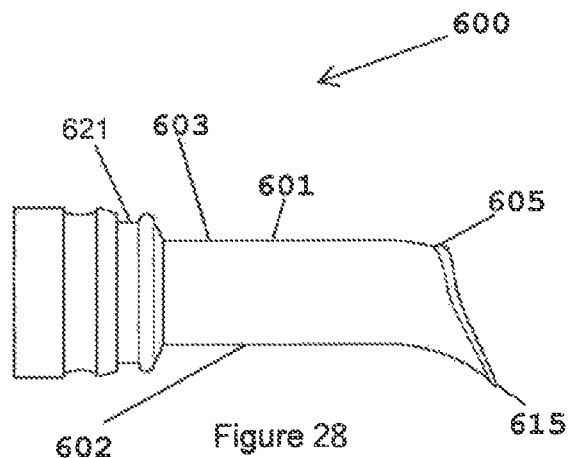
FIGS. 28 to 30 are a side view, plan view and perspective view of a sixth embodiment of a multipurpose oral airway device according to the invention.
Figure 29:
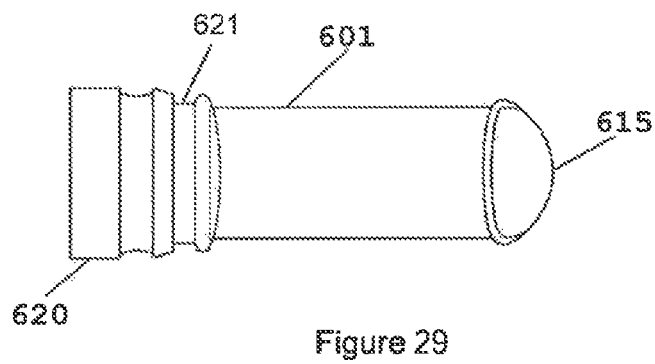
Figure 30:
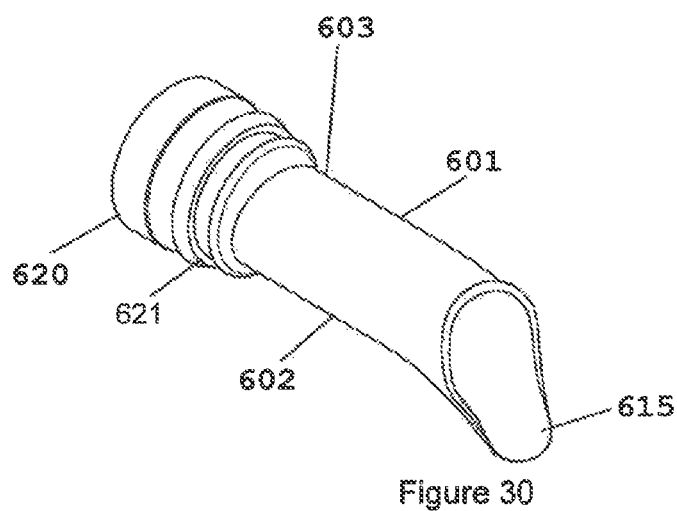
Figure 31:
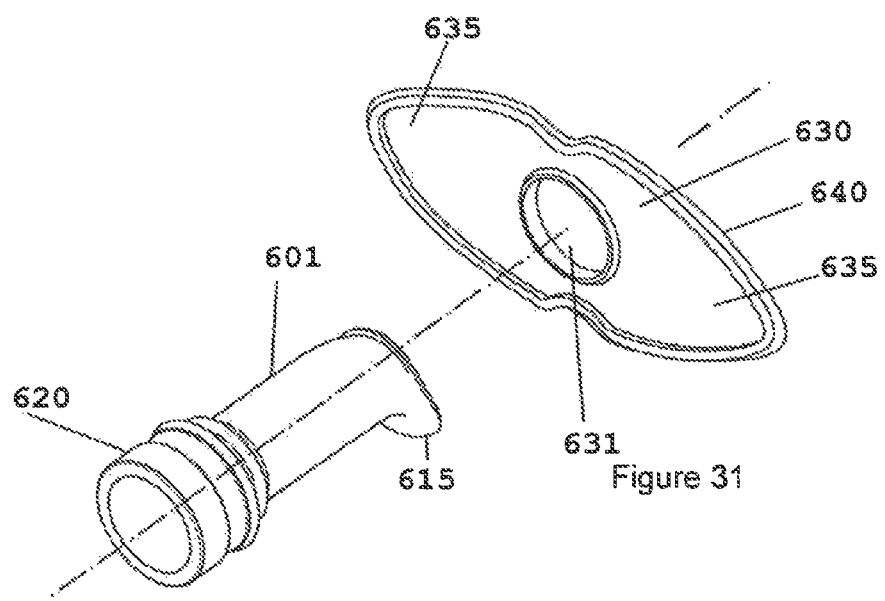
FIG. 31 is a perspective view of the sixth embodiment illustrating the assembly of an intraoral seal onto the device and FIG. 32 is a perspective view of the sixth embodiment showing an ETT locking device being attached.
Figure 32:
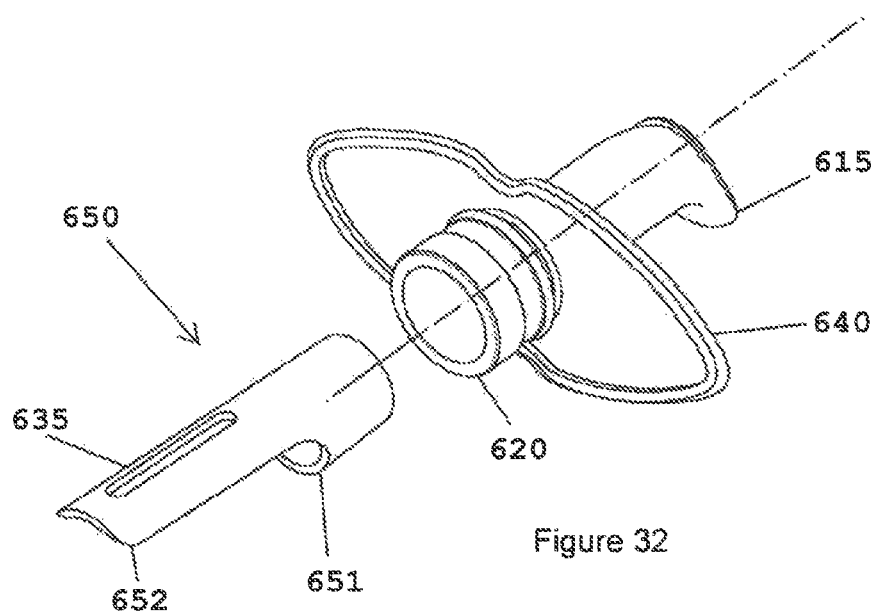
Figure 33:
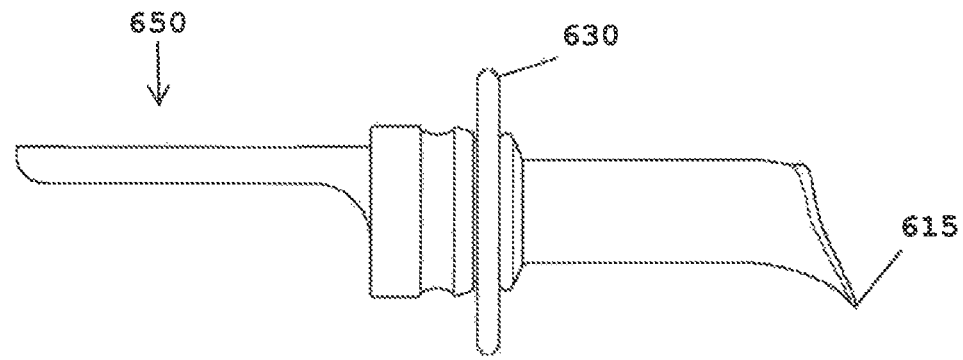
FIGS. 33 and 34 are side and plan views respectively showing the sixth embodiment with the ETT locking device attached.
Figure 34:
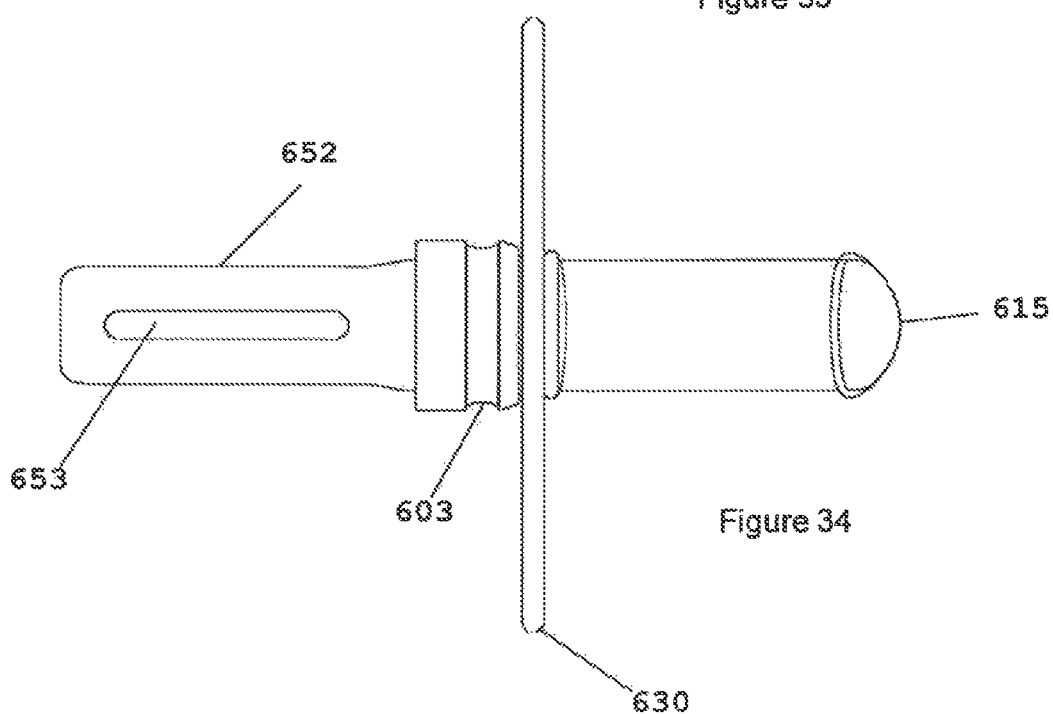
Figure 35:
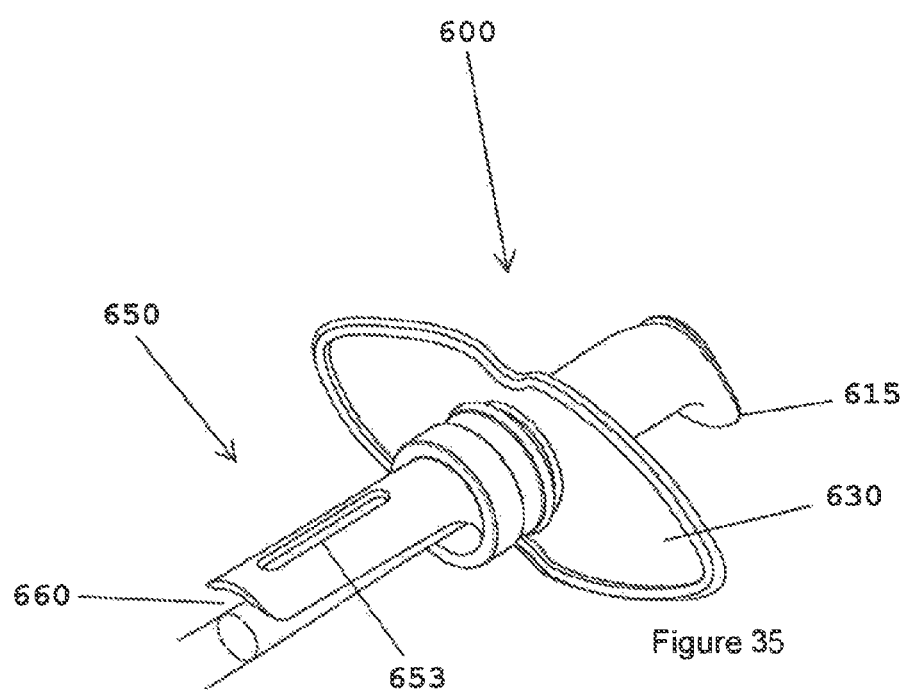
FIG. 35 is a perspective view of the sixth embodiment of the assembled airway device and an intraoral seal, and an endotracheal tube its assembly and illustrating the entire device prior to being inserted into the mouth of a patient.
Figures 39, 40, 41, 42, 43:
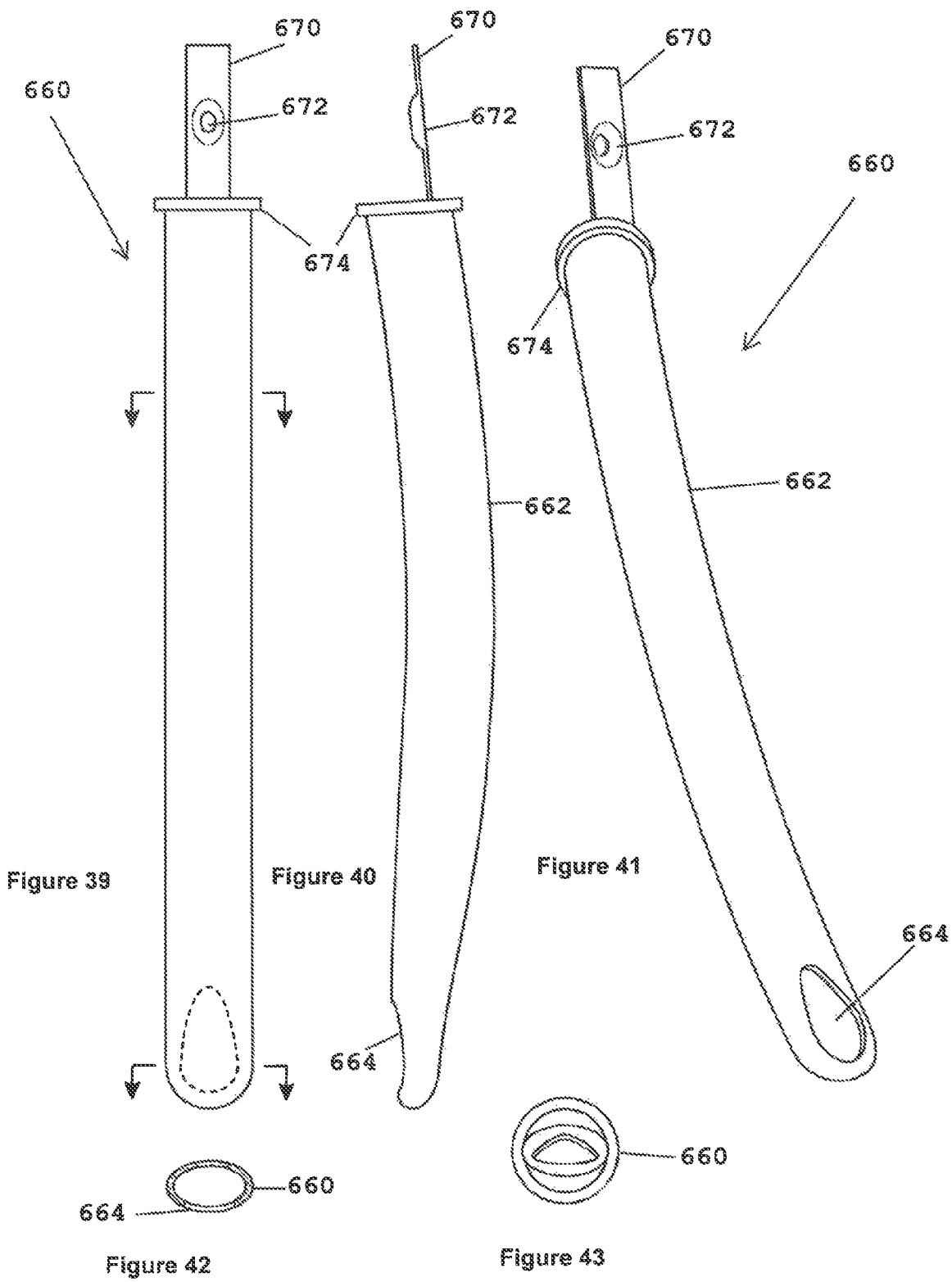
FIGS. 39, 40, 41, 42 and 43 are respectively a series of side views cross-sectional views and end views of the included tube which is used with the fifth embodiment.

The use of the airway device 500 will be explained with reference to FIGS. 25 to 27. To locate the device 500 in the patient's mouth and throat the anaesthetist uses his fingers to press wings 532 of the intraoral seal 530 in a distal direction towards the distal tip 505.

The airway body 501 is then inserted passed the lips L, over the tongue TO until the distal tip 505 and the rim 515 comes to rest in the area between the tongue TO and the epiglottis E. When the anaesthetist pushes the seal 530 passed the lips L, he releases the wings 532, they spring back into their normal orientation between the teeth TE of the patient and the lips L, thus creating a gas tight seal.

In FIGS. 28 to 35, a multipurpose oral airway device of the present invention is shown, generally indicated by the reference numeral 600 which is suitable for an adult and includes a relatively short tubular airway body 601. It has a substantially straight section 602, the proximal end of which is adapted to function as an integral bite block 603, a distal tip 605 and a central channel 606 for accepting an intubation device (not shown). Distal tip 605 facilitates placement of the airway device 600 into a patient's mouth.

Oral airway device 600 also has a substantially oval, butterfly-shaped detachable intraoral seal 630 and connector 620. Airway body 601 is adapted to pass through central aperture 631 of the detachable intraoral seal 630 until the seal is located in groove 621 of connector 620. The intraoral seal 630 extends transverse to the longitude axis of the tubular airway body 601 and narrows down at both sides to rounded points 635. A rim 640 extends about the perimeter of the seal 630 so as to provide the necessary rigidity and stiffness. Two central concave contours 642 (not marked on the drawing) are provided in the rim 640 which aids bending of the seal and location in the patient's mouth.

The underside of the substantially straight section 602 of airway body 601 is provided with a glottal surface which has a horizontal profile when in use it is in relative position with the tongue following the contours of the mouth As shown in FIGS. 32 to 35, an ETT locking device 650 may be attached to connector 620 of multipurpose airway device 600 using a typical push-twist connection. ETT locking device 650 comprises a hollow cylinder 651 for insertion into connector 620 and a finger 652 extending from cylinder 651 and having a slot 635 to which an ETT may be secured with a tie or taped. When ETT locking device 650 is inserted into connector 620, only finger 652 with slot 635 protrudes from connector 620.

Figure 49:
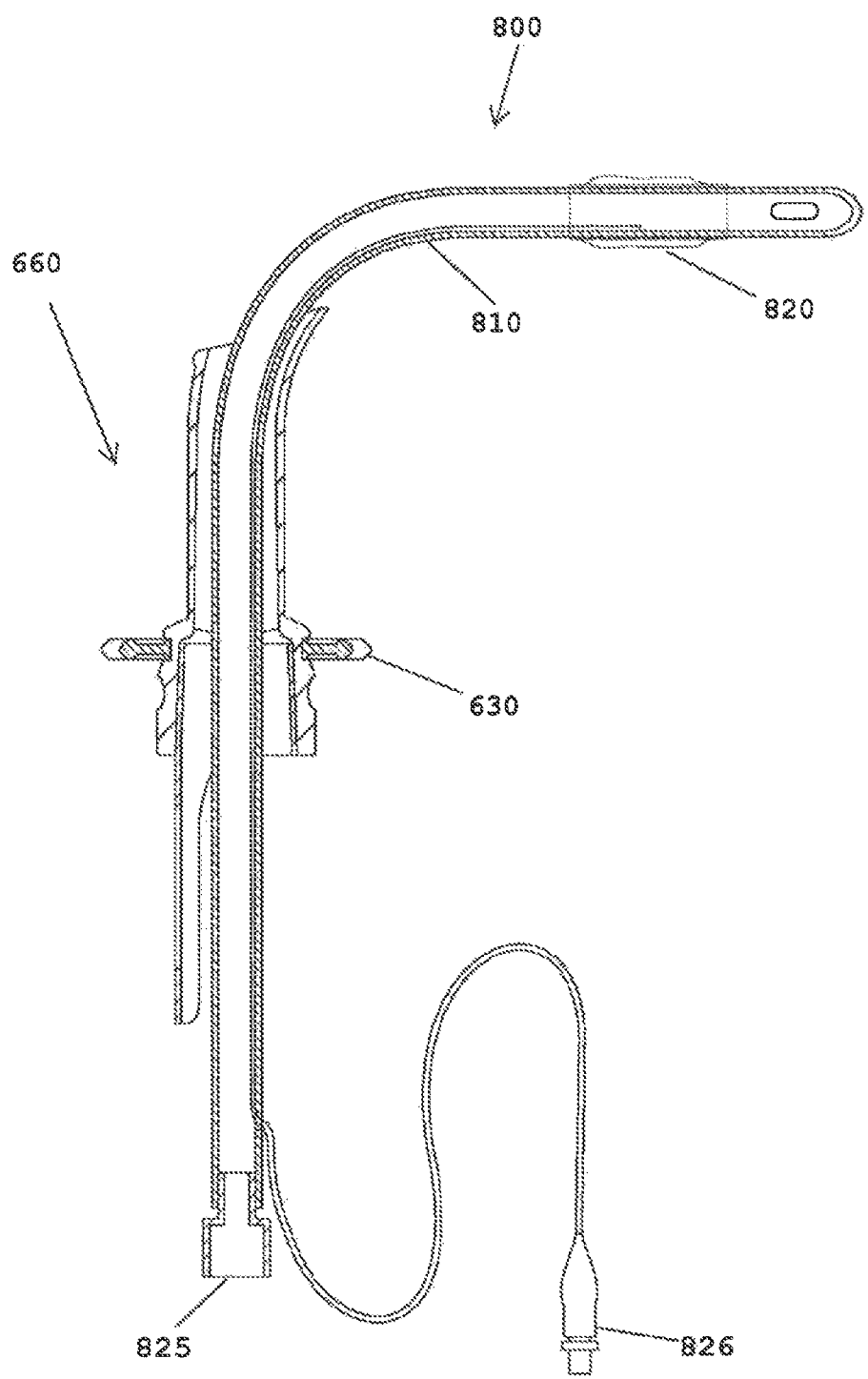
FIG. 49 is a cross-sectional side view of the sixth embodiment extending through an airway device of the invention.
Figure 50:
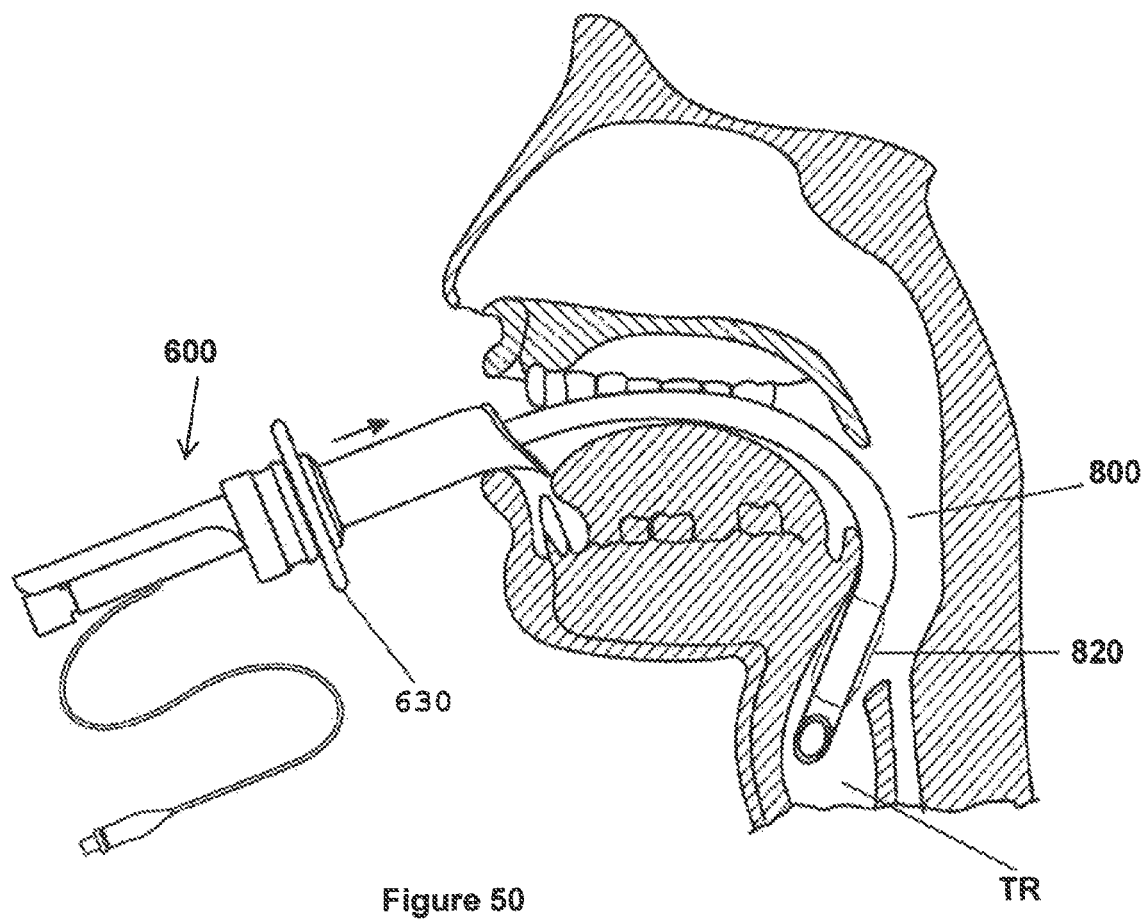
FIG. 50 is a side view of the sixth embodiment as shown in FIG. 49 being inserted into the mouth of the patient.
Figure 51:
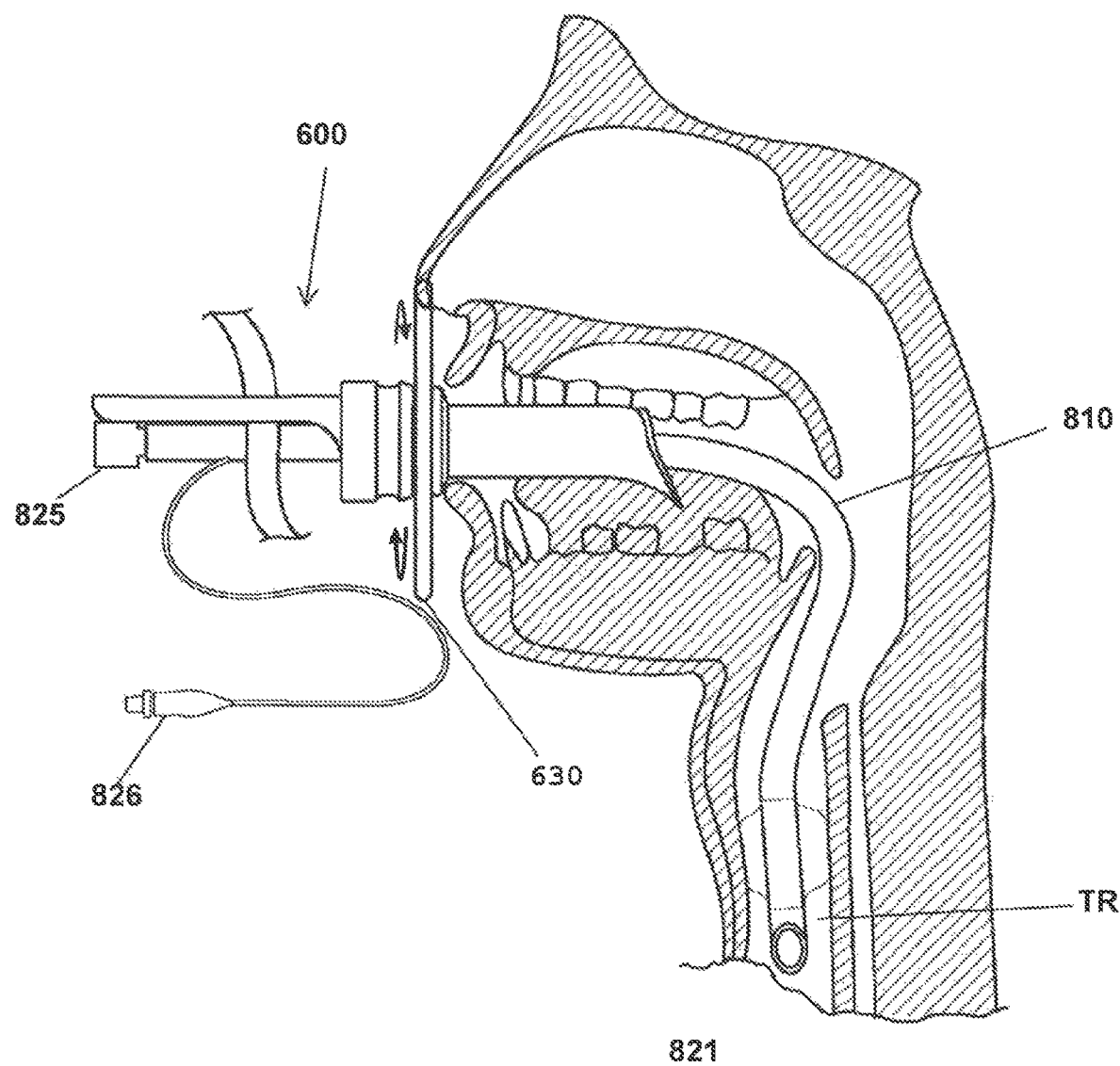
FIG. 51 is a side view of the sixth embodiment as shown in FIGS. 49 and 50 located in position in the mouth of the patient.

FIG. 49 shows airway device 600 with seal 630 and locking device 650 mounted on an endotracheal tube 800. FIG. 50 shows the distal tip of endotracheal tube 800 entering the trachea TR. FIG. 51 shows the cuff of endotracheal tube 800 inflated and sealing the patient's trachea. Seal 630 sits outside the lips with it's long axis facing head to toe so as not to obstruct the mouth.

In use, multipurpose airway device 600 is secured to the patient and an ETT 800 is secured to airway device 600 via ETT locking device 650. This allows for easy intraoperative manipulation of the ETT and avoids the need to remove and reapply any tape to the patient's face, thus making it easier on the patient's skin. In addition, securing the ETT in this way eliminates the risk of kinking the ETT. In the event the ETT needs to be repositioned, the tape or tie securing the ETT 800 to the finger 652 of ETT locking device 650 is easily opened and then secured again after the repositioning. This is especially useful when a double lumen ETT is used, as such double lumen ETTs frequently require repositioning during surgery.

Figure 44:
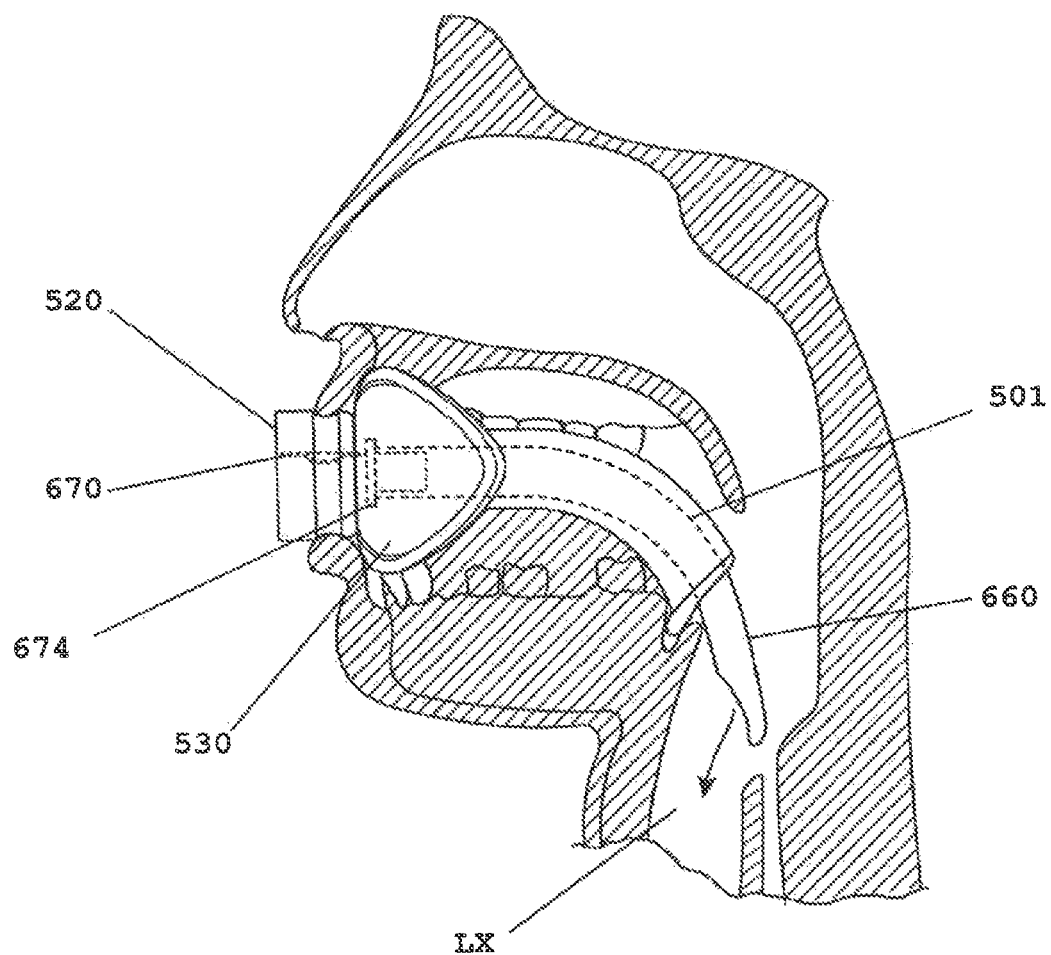
FIG. 44 is a view illustrating the installation of the airway device of the modified fifth embodiment.

The modified fifth embodiment of an oropharyngeal airway device will now be described with reference to FIGS. 36 to 44. The fifth embodiment of airway device 500 is modified by the provision of a separate hypopharyngeal tube 660 fit snugly into the tubular airway body 501 and connector 520. The hypopharyngeal tube 660 is provided with a slightly curved body 662 so as to follow the curvature of the airway device 500. An oval shaped opening 664 is formed at the distal end of the tube 660 and at one side, so that when in situ as shown in FIG. 44, the air and gasses flowing through the tube are directed towards the patient's larynx LX. Provided at the proximal end of the hypopharyngeal tube 660 is a tab 670 which fits completely within the connector 520 of the airway device 500. To remove the tube 660, the anaesthetist grips the tab 670 with his fingers and pulls the tube 660 from the airway device 500. Alternatively he or she may use an instrument to grip the tab 670 or engage in orifice 672 provided in the tab to get a firm engagement and pull the tube. Collar 674 prevents the tube 660 from extending too far into the airway device 500. When the anaesthetic circuit is connected to the connector 520 of the airway device 500, tab 670 is accommodated within the lumen of the anaesthetic circuit connector. When in use hypopharyngeal tube 660 is passed beyond the epiglottis and into the hypopharynx FIG. 44. This makes the combination of airway 500 and hypopharyngeal tube 660 a "hands free" airway.

Figure 45:
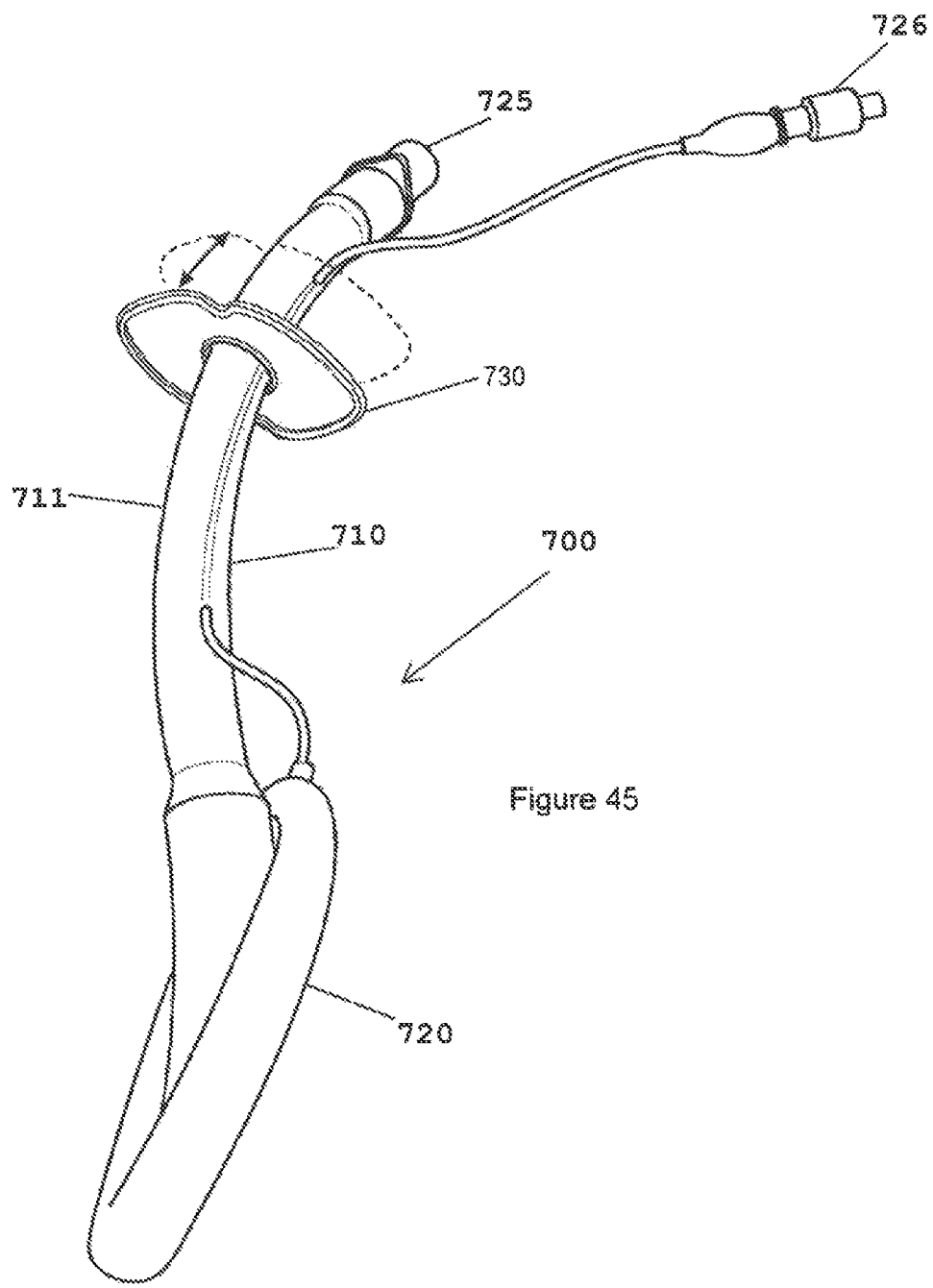
FIG. 45 is a perspective view of an airway device according to the invention including an intraoral seal known as a Laryngeal Mask Airway (LMA) which forms part of a seventh embodiment according to the invention.
Figure 46:
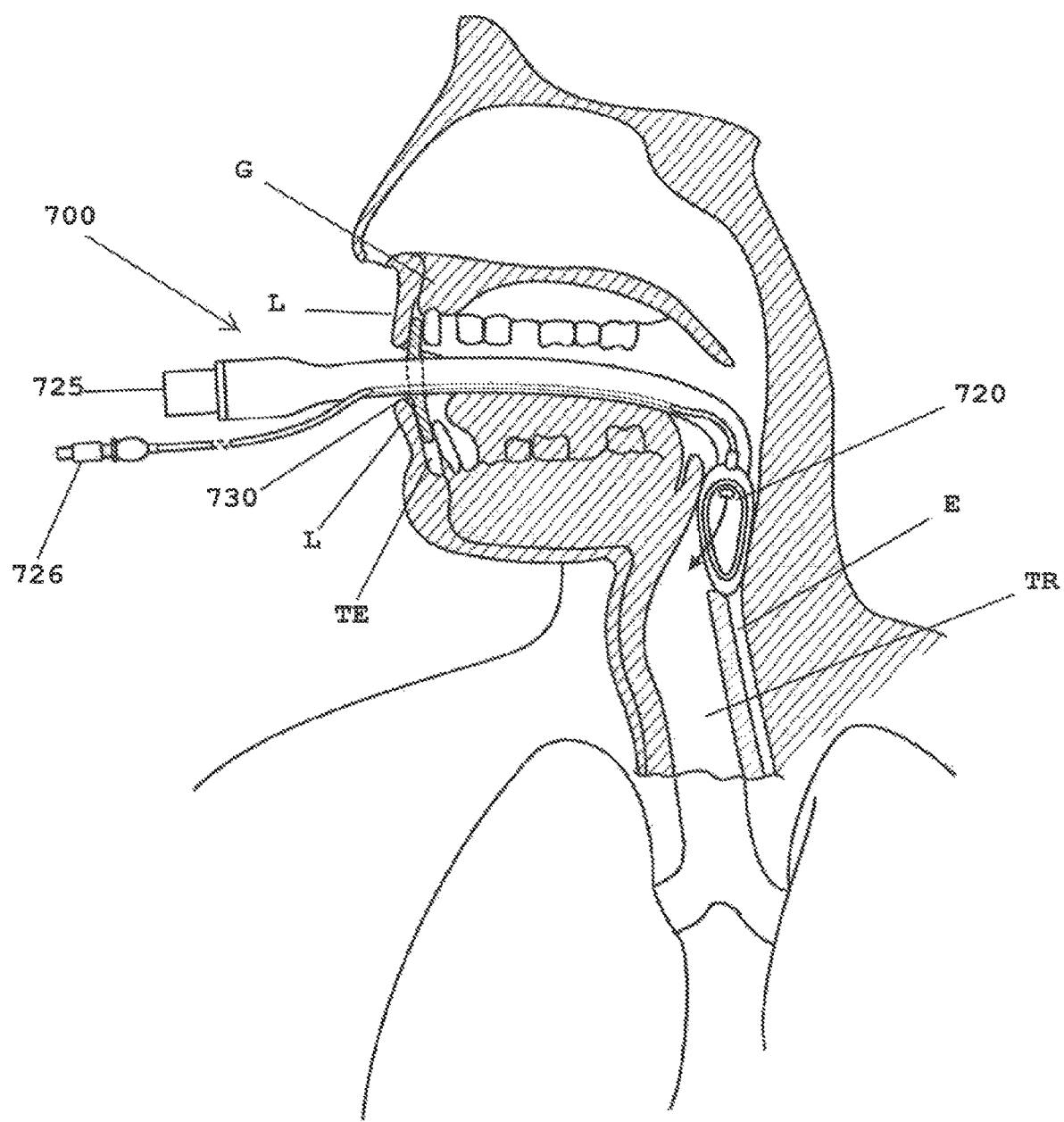
FIG. 46 is a side view of the seventh embodiment arranged in position in the mouth of a patient which acts as a Laryngeal Mask Airway (LMA) positioned behind the larynx in the hypopharynx (also called the laryngopharynx)

The seventh embodiment which is a Laryngeal Mask Airway (LMA) device will now be described with reference to FIGS. 45 and 46. The LMA device 700 having a distal end orifice pad 720 and regular connectors 725 and 726 at the proximal end of the apparatus is modified by the incorporation of a length of the pilot balloon tubing leading to connector 726, into the tubular body 711. The LMA apparatus 710 is modified by the provision of a substantially oval butterfly shaped detachable intraoral seal 730 which fits over main tubular body 711 and is similar in operation as previously described in relation to the fifth embodiment 500. It is installed in a similar manner in the patient as shown in FIG. 46 so that the seal 730 is located between the patient's lips L and teeth TE and gums G. The exit orifice pad 720 is seated on top of the oesophagus E and can direct air and gasses into the larynx.

Figure 47:
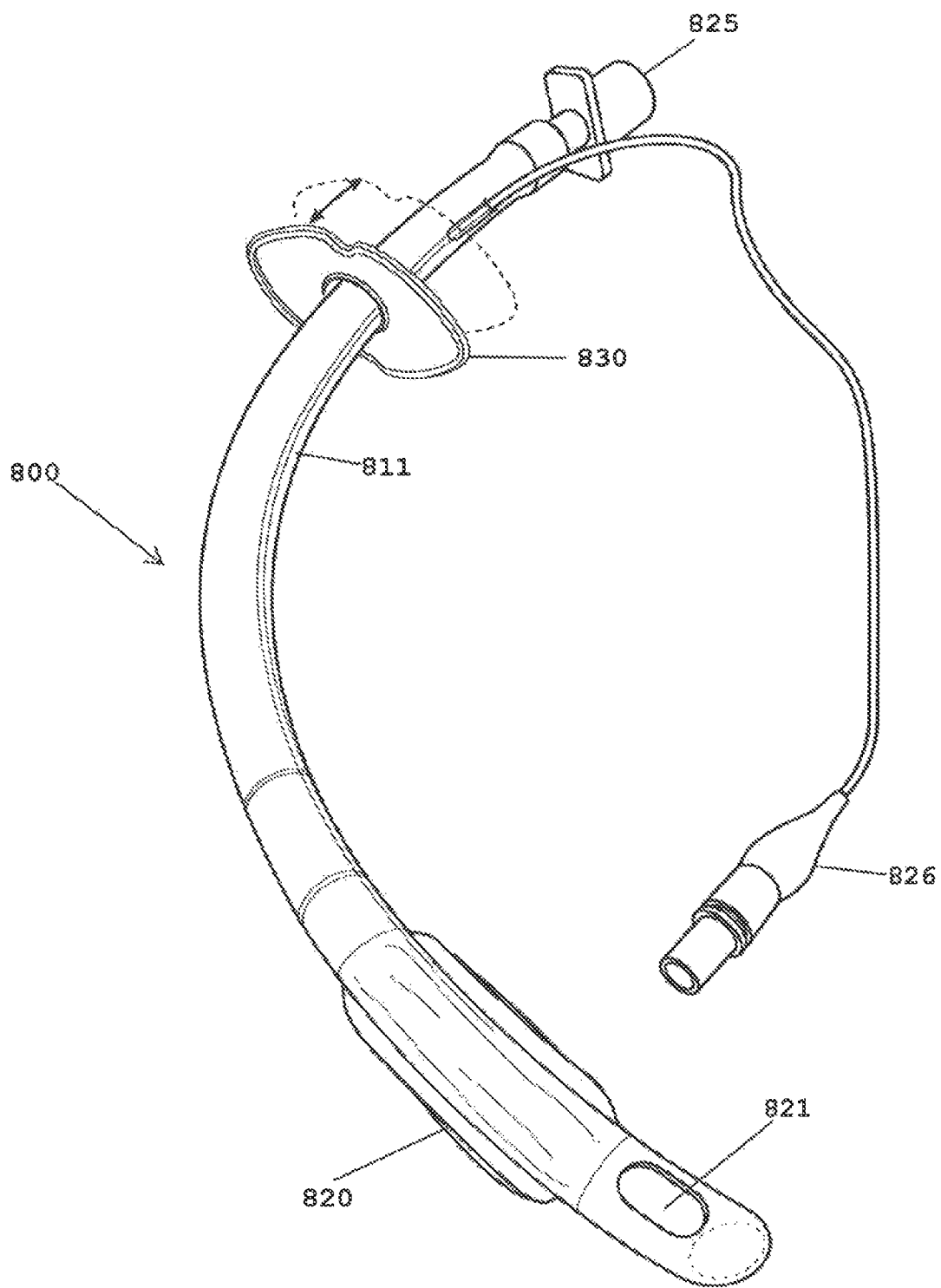
FIG. 47 is a perspective view of an eighth embodiment of an airway device according to the invention including an intraoral seal which functions as an Endotracheal tube (ETT)
Figure 48:
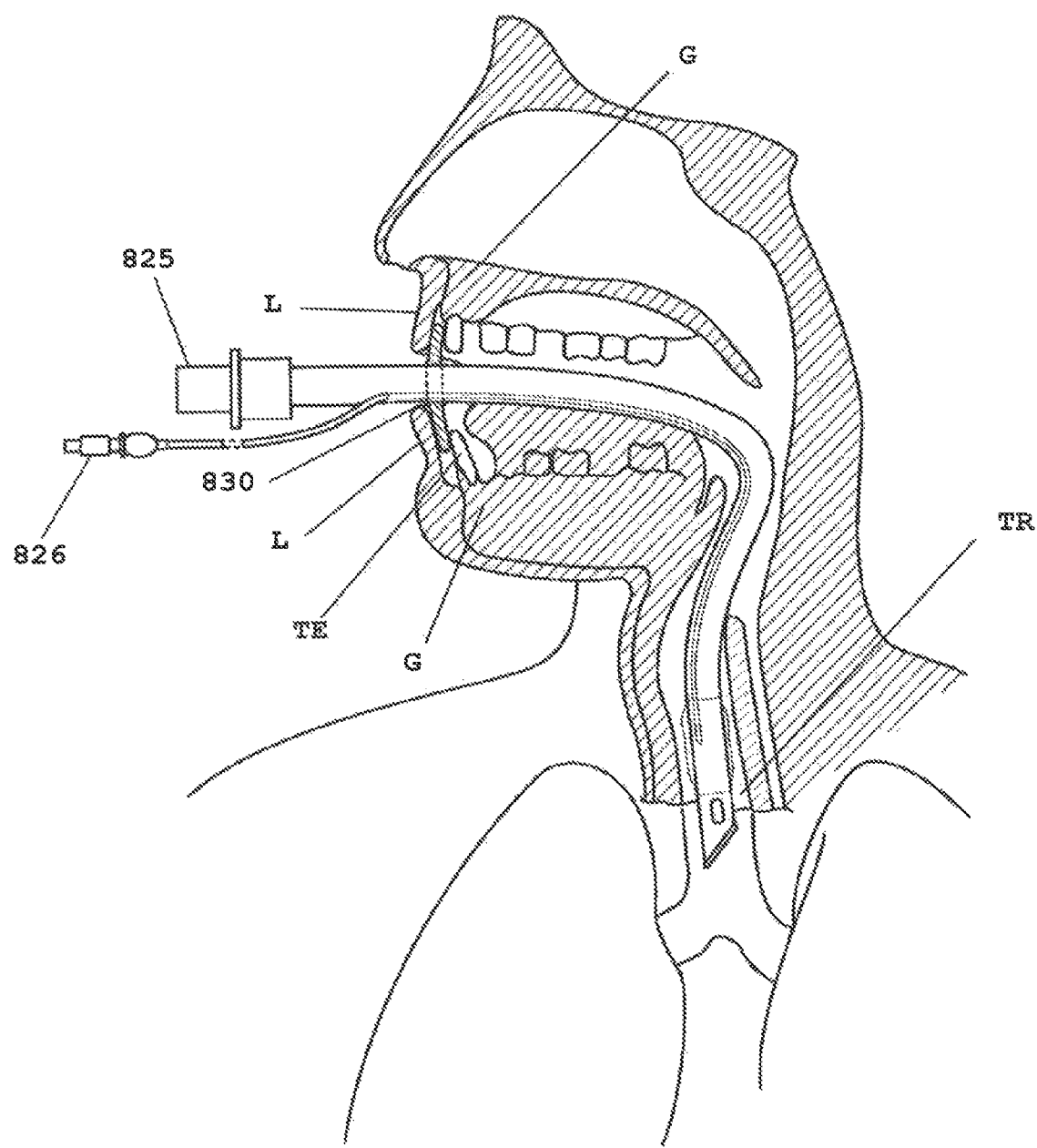
FIG. 48 is a side view of the eighth embodiment arranged in position in the mouth and larynx and trachea of a patient.

The eighth embodiment which functions as an Endotracheal Tube (ETT) will be described with reference to FIGS. 47 and 48. In FIGS. 47 and 48 as shown, an ETT tube 800 having an inflatable cuff 820 at the distal end and regular connectors 825 and 826. An intraoral seal 830 fits over the main tubular body 811 and when in situ is used to form a seal between the patient's lips L and teeth TE and gums G. The inflatable cuff 820 is located in the patient's trachea TR and when inflated seals the trachea. Gases are primarily delivered out of the terminal opening. Orifice 821 on an ETT, called a Murphy eye, is there in case the distal oriface is blocked because the ETT is in too far in an endobronchial position. FIGS. 50 and 51 illustrate the use of the ETT tube 800 with the airway device 600. The seal 630 is rotated 90° about the longitudinal axis of the device so that the seal is located outside the patient's mouth and facing head to toe so as not to obstruct the mouth. The inflatable cuff 820 provides the necessary sealing function.

It will of course be understood that the invention is not limited to the specific details as herein described, which are given by way of example only, and that various alterations and modifications are possible without departing from the scope of the invention as defined in the appended claims.

The invention claimed is:

1. A multipurpose oral airway device adapted for insertion into the mouth of a patient, said airway device comprising:
   (a) an elongate, tubular airway body of substantially elliptical or substantially circular cross-section, the airway body having:
   a substantially straight section, and a proximal end which is adapted to function as an integral bite block;
   a curved distal section with a distal tip, wherein the curved distal section is configured to substantially conform to the curvature of a patient's palate but does not extend into the patient's pharynx, wherein the distal tip has a downwardly offset rim that aids placement of the airway device into the mouth and spreads pressure across a back of a tongue; and
   a central channel for the passage of oxygen and anaesthetic gasses and for accepting an intubation device and for accepting an endoscopic device;
   (b) a substantially oval-shaped detachable intraoral self retaining and self sealing plate that is configured to dynamically form an air-tight seal between the airway device and the mouth from inside the mouth having a central aperture for receiving the airway body; and
   (c) a connector for facilitating attachment of breathing or anaesthesia equipment thereto, wherein the connector is attached to the proximal end of the airway body and has a groove on its external surface, wherein the groove forms a circular channel for accepting the detachable intraoral plate;
   wherein the plate which is essentially flat with a reinforced rim around the perimeter resists deformation with a second rim surrounding the central aperture,
   wherein the plate is a one piece construction of polyvinyl chloride, polyurethane, silicone or some other elastomeric material possessing properties of elasticity, resilience and flexibility, wherein the plate is self retaining and self sealing, which elasticity allows the plate to be fitted and retained in position on airway devices and allows the plate to be compressed between thumb and forefinger for placement inside the cheeks of the patient, and when released by the thumb and forefinger to be compressed by the cheeks and forced to follow a curved contour of the inside of the cheeks and dynamically seal the mouth from the inside and a sealing effect is enhanced during positive pressure ventilation by a gas pressure pushing the plate against the inside of the mouth;
   wherein between the reinforced rim around the perimeter of the plate and the second rim surrounding the central aperture, the plate is soft and flexible, wherein the plate is configured to seal seals the mouth opening by adhering to a soft moist and smooth inner mucosa of the cheeks and lips;
   wherein the plate does not seal a large opening between the upper and lower jaws but rather seals the mouth of the patient due to the width of the vestibule of the mouth being much greater than the width of the mouth opening and allowing for the width of the plate to be much greater than the maximum width of the mouth opening, whereby the corners of the mouth retain the multipurpose airway device and are sealed and no gas leaks from the corners of the mouth, whereby the multipurpose oral airway device is self retaining, self sealing and hands free.

2. The multipurpose airway device as claimed in claim 1, wherein the detachable intraoral self retaining and self sealing plate is made of plastic, rubber, silicone, polyvinyl chloride, or other flexible material.

3. The multipurpose airway device as claimed in claim 1 in which the self retaining and self sealing intraoral plate is generally flat and has a much greater cross-sectional area than the mouth opening, and is shaped to aid placement.

4. The multipurpose airway device as claimed in claim 1 in which the detachable, flexible, self-sealing and self retaining plate is essentially flat with a greater cross-sectional area than the mouth opening, with a shape corresponding to the mouth opening when the mouth is open and each end is arrow shaped like the corner of the mouth when open to aid placement.

5. The multipurpose airway device as claimed in claim 1 in which the plate is self-retaining as a result of its shear modulus (modulus of rigidity) which enables the plate to initially deform to the curvature of inside the cheeks of the patient but resists further deformity thereby becoming progressively more difficult to deform, due to the gradient of its stress-strain curve increasing with stress, and therefore resists displacement from the mouth of the patient.

6. The multipurpose airway device as claimed in claim 1 in which the plate is self-sealing due to its resilience in that it is quickly and constantly trying to return to its original shape, so that it is configured to dynamically form the air-tight seal inside of the mouth of the patient in that it is configured to continuously follow a variation in the surface of the mouth that it is sealing, when the mouth may undergo small changes in size and shape during the different phases of the respiratory cycle, whereby the plate maintains the air-tight seal as the mouth opening changes size and shape and the sealing effect is enhanced during periods of positive pressure ventilation by the gas pressure forcing the plate against the inside of the cheeks.

7. The multipurpose airway device as claimed in claim 1 in which the elastomeric material of the plate has a high elastic limit but does not display plasticity, so that the lips of the patient function as a purse string largely because of the bulk of the orbicularis oris muscle even when it is relaxed and not contracting, whereby the reinforced rim around the perimeter of the plate resists distortion and when in place in the vestibule of the mouth to sit outside the orbicularis oris muscle and especially at the corners of the mouth and so retains the plate even during positive pressure breaths and the plate is further supported in position in the vestibule of the mouth between the lips and cheeks, gums and teeth of the patient by the airway body traversing and firmly gripped in the central aperture of the plate.

8. The multipurpose airway device as claimed in claim 1 in which the plate has a cut-out in the midline at a top and bottom of the plate to accommodate a top and a bottom frenulum.

9. The multipurpose airway device as claimed in claim 1 in which the plate contributes to jaw thrust because it resists deformation, whereby when the plate is in position in the vestibule of the mouth of the patient it is forced by the cheeks to adopt the contour of the inside of the cheeks, and in resisting deformation because the upper jaw is fixed and not mobile the plate pulls forward the lower jaw and this is enhanced during positive pressure ventilation when gas under pressure emitting from the distal end of the airway device pushes against the plate from the inside.

10. The multipurpose airway device as claimed in claim 1, wherein the airway body is made of a polymer selected from among medical grade polyethylene, polypropylene and polycarbonate.

11. The multipurpose airway device as claimed in claim 1, wherein the groove for accepting the detachable intraoral seal is adapted such that the detachable intraoral seal is configured to be rotated with respect to the airway body.

12. The multipurpose airway device as claimed in claim 1, wherein the multipurpose airway device is of a size for a mouth of a child patient and the tubular airway body has a circular cross-section.

13. The multipurpose airway device as claimed in claim 12, wherein an internal diameter of the tubular airway body is in a range of from approximately 7 mm to approximately 40 mm.

14. The multipurpose airway device as claimed in claim 1, wherein the multipurpose airway device is of a size for a mouth of an adult patient and the tubular airway body has an elliptical cross-section.

15. The multipurpose airway device as claimed in claim 14, wherein an external conjugate diameter of the tubular airway body is in a range of from approximately 15 mm to approximately 50 mm.

16. The multipurpose airway device as claimed in claim 14, wherein an external transverse diameter of the tubular airway body is in a range of from approximately 15 mm to approximately 50 mm.

17. The multipurpose airway device as claimed in claim 15, wherein an external transverse diameter of the tubular airway body is in a range of from approximately 15 mm to approximately 50 mm.

18. The multipurpose airway device as claimed in claim 14, wherein an internal diameter of the tubular airway body is in a range of from approximately 10 mm to approximately 45 mm.

19. The multipurpose airway device as claimed in claim 14, wherein the connector has a second groove which provides a circular channel for accepting tie material.

20. An endotracheal tube (ETT) locking device for attachment to the multipurpose airway device defined in claim 1, wherein the locking device comprises a hollow cylinder for insertion into the connector of the multipurpose airway device and a finger, the finger extending from the cylinder and having a slot configured to secure an ETT by adhesive tape or by a tie.

21. The multipurpose airway device as claimed in claim 1, in which a separate hypopharyngeal tube is provided to fit snugly into the tubular airway body and the connector and to protrude beyond the proximal end of the tubular airway body so that in use the tube can be passed beyond a patient's epiglottis and into the hypopharynx thereby making the device a hands free airway.

22. The multipurpose airway device as claimed in claim 21, in which the hypopharyngeal tube has an elongate curved body adapted to follow the curvature of the airway device and an opening is provided at a distal end of the hypopharyngeal tube and at one side thereof so that, in use, air and gasses are directed towards the patient's larynx.

23. The multipurpose airway device as claimed in claim 21 in which a gripping tab is provided at a proximal end of the hypopharyngeal tube, the gripping tab being adapted to fit completely within the connector of the airway device.

24. The multipurpose airway device as claimed in claim 22 in which a gripping tab is provided at a proximal end of the hypopharyngeal tube, the gripping tab being adapted to fit completely within the connector of the airway device.

25. The multipurpose airway device as claimed in claim 24, in which the gripping tab is provided with a locating orifice.

26. A multipurpose oropharyngeal airway device adapted for insertion into a mouth of a patient, said airway device comprising:
(a) an elongate, tubular airway body of substantially elliptical or substantially circular cross-section, the tubular airway body having:
a substantially straight section, and a proximal end which is adapted to function as an integral bite block;
a curved distal section that is configured to substantially conform to the curvature of a part of the patient's pharynx between the soft palate and an upper edge of the epiglottis, the curved distal section having a distal tip with a tear-drop shaped downwardly offset rim that aids placement of the airway device into the mouth of the patient and spreads pressure across a back of a tongue; and
a central channel for passage of oxygen and anaesthetic gasses and for accepting an intubation device and for accepting an endoscopic device;
(b) a substantially oval-shaped detachable intraoral self retaining and self sealing plate for dynamically sealing the mouth from inside the mouth having a central aperture for receiving the tubular airway body; and
(c) a connector for facilitating attachment of breathing or anaesthesia equipment thereto, wherein the connector is attached to the proximal end of the tubular airway body and has a groove on its external surface, wherein the groove forms a circular channel for accepting the detachable intraoral plate;
wherein the plate which is essentially flat with a reinforced rim around the perimeter resists deformation with a second rim surrounding the central aperture,
wherein the plate is a one piece construction of polyvinyl chloride, polyurethane, silicone or some other elastomeric material possessing properties of elasticity, resilience and flexibility, so that the plate is self retaining and self sealing, which elasticity allows the plate to be fitted and retained in position on airway devices and allows the plate to be compressed between thumb and forefinger for placement inside the cheeks of the patient, and when released by the thumb and forefinger to be compressed by the cheeks and forced to follow a curved contour of the inside of the cheeks and dynamically seal the mouth from the inside and a sealing effect is enhanced during positive pressure ventilation by a gas pressure pushing the plate against the inside of the mouth;

wherein between the reinforced rim around the perimeter of the plate and the second rim surrounding the central aperture, the plate is soft and flexible, wherein the plate is configured to seal the mouth opening by adhering to a soft moist and smooth inner mucosa of the cheeks and lips;

wherein the plate does not seal a large opening between the upper and lower jaws but rather seals the mouth of the patient due to the width of the vestibule of the mouth being much greater than the width of the mouth opening and allowing for the width of the plate to be much greater than the maximum width of the mouth opening, whereby the corners of the mouth retain the multipurpose airway device and are sealed and no gas leaks from the corners of the mouth, whereby the multipurpose oropharyngeal airway body is self retaining, self sealing and hands free.

27. The multipurpose airway device as claimed in claim 1, wherein the downwardly offset rim is tear-dropped shape and positioned around an opening of the distal tip.

* * * * *